United States Patent [19]
Obata et al.

[11] Patent Number: 5,639,771
[45] Date of Patent: Jun. 17, 1997

[54] OXAZOLINE DERIVATIVE, PROCESS FOR PREPARING THE SAME AND AGRICULTURAL AND HORTICULTURAL CHEMICAL FOR CONTROLLING NOXIOUS ORGANISMS CONTAINING THE SAME

[75] Inventors: Tokio Obata; Katsutoshi Fujii; Shoji Shikita; Kouichi Goka, all of Ube, Japan

[73] Assignee: Ube Industries, Ltd., Yamaguchi-ken, Japan

[21] Appl. No.: 348,921

[22] Filed: Nov. 25, 1994

[30] Foreign Application Priority Data

Nov. 26, 1993 [JP] Japan .................... 5-296273

[51] Int. Cl.$^6$ .................... A01N 43/76
[52] U.S. Cl. .................... 514/374; 548/237; 548/239; 564/158; 546/271.4; 514/330; 544/137
[58] Field of Search .................... 514/374; 548/237, 548/239

[56] References Cited

U.S. PATENT DOCUMENTS

| | | | |
|---|---|---|---|
| 4,225,336 | 9/1980 | Fory et al. | 548/237 |
| 4,977,171 | 12/1990 | Suzuki et al. | 548/237 |
| 5,141,948 | 8/1992 | Miyamoto et al. | 548/237 |
| 5,411,979 | 5/1995 | Hirose et al. | 548/237 |
| 5,466,703 | 11/1995 | Kudoh et al. | 514/374 |

FOREIGN PATENT DOCUMENTS

| | | |
|---|---|---|
| 0553623 | 8/1983 | European Pat. Off. . |
| 0345775 | 12/1989 | European Pat. Off. . |
| 0432661 | 6/1991 | European Pat. Off. . |
| 0553623A1 | 8/1993 | European Pat. Off. . |
| 0594179 | 4/1994 | European Pat. Off. . |
| 57-501962 | 11/1982 | Japan . |
| 2-85268 | 3/1990 | Japan . |
| 2-304069 | 12/1990 | Japan . |
| 3-232867 | 10/1991 | Japan . |
| 4-89484 | 3/1992 | Japan . |
| 4-217673 | 8/1992 | Japan . |
| 5-1060 | 1/1993 | Japan . |
| 6-48907 | 2/1994 | Japan . |

OTHER PUBLICATIONS

"A Biorationally Synthesized Octopaminergic Insecticide: 2-(4-Chloro-o-toluidino)-2-oxazoline", Jennings et al., Pesticide Biochemistry and Physiology 30, pp. 190–197 (1988).

*Primary Examiner*—Donald G. Daus
*Attorney, Agent, or Firm*—Finnegan, Henderson, Farabow, Garrett & Dunner, L.L.P.

[57] ABSTRACT

Disclosed are an oxazoline compound represented by the formula (I):

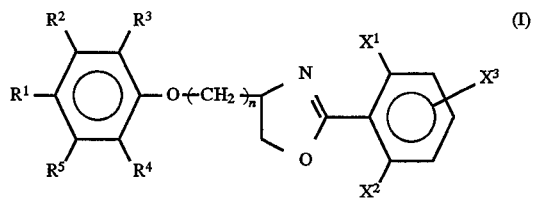

wherein $R^1$ represents halogen, hydrogen, alkyl, alkoxy, haloalkyl, haloalkoxy, phenyl, phenoxy, benzyl, benzyloxy, pyridyloxy, pyridylmethyloxy, alkoxy-substituted alkyl, nitro, cyanomethyloxy, haloalkylsulfonyloxy, alkylsulfonyloxy, or alkylthio; $R^2$ represents hydrogen, halogen, alkyl, haloalkyl, alkoxy, alkylthio, or haloalkoxy; $R^1$ and $R^2$ may be combined to form a saturated or unsaturated 6-membered ring with oxygen; $R^3$ represents hydrogen, halogen or alkoxy; $R^4$ represents hydrogen, alkyl, or halogen; $R^5$ represents hydrogen, halogen, or alkyl; $X^1$ represents halogen, alkyl, haloalkyl, or alkoxy; $X^2$ represents halogen, hydrogen, or alkoxy; $X^3$ represents hydrogen or halogen; and n represents an integer of 2 to 5;

an amidoethyl halide derivative used for synthesis of the same, a process for preparing the same, and an agricultural and horticultural chemical for controlling noxious organisms comprising the same as an active ingredient.

9 Claims, No Drawings

OXAZOLINE DERIVATIVE, PROCESS FOR PREPARING THE SAME AND AGRICULTURAL AND HORTICULTURAL CHEMICAL FOR CONTROLLING NOXIOUS ORGANISMS CONTAINING THE SAME

BACKGROUND OF THE INVENTION

This invention relates to a novel oxazoline derivative which is an agricultural and horticultural chemical for controlling noxious organisms useful as an insecticide, an acaricide and a fungicide.

As an oxazoline derivative similar to the oxazoline derivative of the present invention, the following compounds have been known.

(1) In Pesticide Biochemistry and Physiology 30, pp. 190 to 197, it has been described that a compound represented by the following formula:

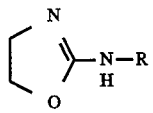

wherein R represents a phenyl group, a cyclohexyl group or a benzyl group; provided that the definition of the above R is limited only to the above formula,
is effective as an insecticide and an acaricide.

(2) In Japanese Provisional Patent Publication No. 501962/1982 (which corresponds to European Patent Publication No. 0 078 804 A), it has been described that a compound represented by the following formula:

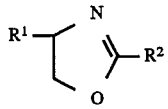

wherein $R^1$ represents an alkyl group having 1 to 6 carbon atoms which may be substituted by a hydroxy group, an alkoxycarbonyl group having 1 to 4 carbon atoms or the like; $R^2$ represents an aryl group or the like; provided that the definitions of the above $R^1$ and $R^2$ are limited only to the above formula,
is effective as an medical intermediate.

(3) In Japanese Provisional Patent Publication No. 85268/1990 (which corresponds to U.S. Pat. No. 4,977,171), it has been described that a compound represented by the following formula:

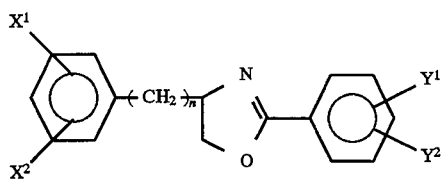

wherein $X^1$ and $X^2$ each represent a hydrogen atom, an alkyl group, an alkoxy group, a halogen atom, a trifluoromethyl group or a trifluoromethoxy group; $Y^1$ and $Y^2$ each represent a hydrogen atom, an alkyl group, a halogen atom or the like; n represents 0 or 1; excluded is the case where $Y^1$ and $Y^2$ are an optional combination of substituents selected from a hydrogen atom and a halogen atom when n is 0 and both of $X^1$ and $X^2$ are hydrogen atoms or when n is 1 and both of $X^1$ and $X^2$ are an optional combination of substituents selected from a hydrogen atom and a halogen atom (other than an iodine atom); provided that the definitions of the above $X^1$, $X^2$, $Y^1$, $Y^2$ and n are limited only to the above formula,
is effective as an insecticide and an acaricide.

(4) In Japanese Provisional Patent Publication No. 304069/1990, it has been described that a compound represented by the following formula:

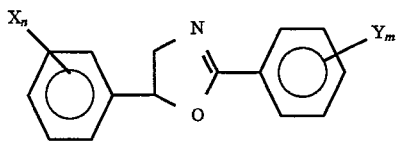

wherein X represents a lower alkyl group, a lower alkoxy group, a halogen atom or a $CH_3$ group; Y represents a halogen atom or the like; m and n each represent an integer of 0 to 2; provided that the definitions of the above X, Y, m and n are limited only to the above formula,
is effective as an insecticide and an acaricide.

(5) In Japanese Provisional Patent Publication No. 232867/1991 (which corresponds to U.S. Pat. No. 5,141,948), it has been described that a compound represented by the following formula:

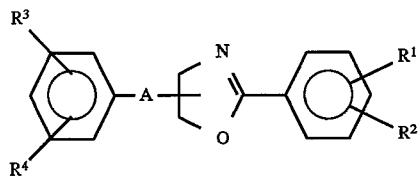

wherein $R^1$ and $R^2$ each represent a halogen atom or the like; $R^3$ represents a hydrogen atom, a halogen atom, a lower alkyl group or a lower alkoxy group; $R^4$ represents an alkyl group having 7 or more carbon atoms, an alkoxy group having 7 or more carbon atoms, an alkylthio group, a lower alkoxy-lower alkyl group, a lower alkoxy-lower alkoxy group, an alkenyloxy group having 3 or more carbon atoms, a lower alkynyloxy group, a tri(lower alkyl)silyl group, a cycloalkyl group which may be optionally substituted by a lower alkyl group or

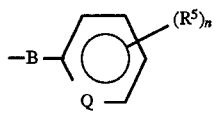

(where B represents a direct bond, an oxygen atom, a lower alkylene group, a lower alkyleneoxy group, a lower alkylenedioxy group or a di(lower alkyl)silyl group; Q represents CN or N; n represents an integer of 0 to 5; and n substituents RSs represent a halogen atom, an alkyl group, an alkoxy group, a lower haloalkyl group, a lower haloalkoxy group or a tri(lower alkyl) silyl group); A represents a direct bond or an alkylene group; provided that the definitions of the above $R^1$ to $R^5$, B, Q, n and A are limited only to the above formula,
is effective as an insecticide and an acaricide.

(6) In Japanese Provisional Patent Publication No. 89484/1992, it has been described that a compound represented by the following formula:

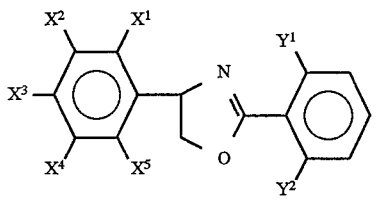

wherein $X^1$ represents a hydrogen atom, a fluorine atom, a chlorine atom, a lower alkyl group or a lower alkoxy group; $X^2$, $X^3$ and $X^4$ each represent a hydrogen atom, a fluorine atom, a chlorine atom, a bromine atom, a lower alkyl group or a lower alkoxy group; $X^5$ represents a hydrogen atom, a fluorine atom, a methyl group or a methoxy group; the case where 3 or more of $X^1$ to $X^5$ are hydrogen atoms is excluded; $Y^1$ represents a hydrogen atom, a fluorine atom or a halogen atom; and $Y^2$ represents a fluorine atom or a chlorine atom; provided that the definitions of the above $X^1$ to $X^5$, $Y^1$ and $Y^2$ are limited only to the above formula, is effective as an insecticide and an acaricide.

(7) In Japanese Provisional Patent Publication No. 217673/1992, it has been described that a compound represented by the following formula:

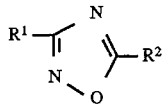

wherein $R^1$ represents a phenoxymethyl group which may be substituted by a halogen atom, an alkyl group, a trifluoromethyl group, an alkoxy group or a thioalkoxy group, or the like; $R^2$ represents a phenyl group which may be substituted by a halogen atom, or the like; provided that the definitions of the above $R^1$ and $R^2$ are limited only to the above formula, is effective as an insecticide and an acaricide.

(8) In Japanese Provisional Patent Publication No. 1060/1993, it has been described that a compound represented by the following formula (A):

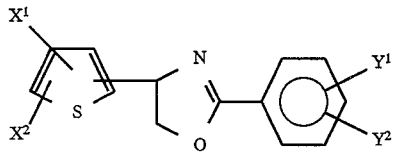

wherein $X^1$ and $X^2$ each represent a hydrogen atom, an alkyl group, an alkoxy group, a halogen atom, a trifluoromethyl group, a trifluoromethoxy group or a group of the formula (B); $Y^1$ and $Y^2$ each represent a halogen atom or the like; provided that the definitions of the above $X^1$, $X^2$, $Y^1$ and $Y^2$ are limited only to the formula (A),

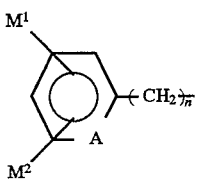

wherein $M^1$ and $M^2$ each represent a hydrogen atom, an alkyl group, an alkoxy group, a halogen atom, a trifluoromethyl group or a trifluoromethoxy group; A represents $CH_2$ or a nitrogen atom; n represents 0 or 1; provided that the definitions of the above $M^1$, $M^2$, A and n are limited only to the formula (B), is effective as an insecticide and an acaricide.

(9) In Japanese Provisional Patent Publication No. 271206/1993, (which corresponds to European Patent Publication No. 0 553 623 A), it has been described that a compound represented by the following formula (C):

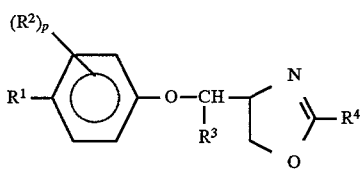

wherein $R^1$ represents a hydrogen atom, a halogen atom, an alkyl group having 1 to 16 carbon atoms, an alkoxyalkyl group having 2 to 16 carbon atoms, an alkoxy group having 1 to 16 carbon atoms, a cycloalkyl group having 3 to 16 carbon atoms, an alkylcycloalkyl group having 4 to 16 carbon atoms, a cycloalkoxy group having 5 to 16 carbon atoms, an alkoxycycloalkoxy group having 5 to 16 carbon atoms, a group of the formula (D) or the like; $R^2$ represents a hydrogen atom, a halogen atom, an alkyl group having 1 to 3 carbon atoms, an alkoxy group having 1 to 3 carbon atoms or an alkylthio group having 1 to 3 carbon atoms; p represents an integer of 1 to 4; $R^3$ represents a hydrogen atom or the like; $R^4$ represents a group of the formula (E); provided that the definitions of the above $R^1$ to $R^4$ and p are limited only to the formula (C),

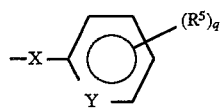

wherein $R^5$ represents a hydrogen atom, a halogen atom, an alkyl group having 1 to 8 carbon atoms, an alkoxyalkyl group having 2 to 8 carbon atoms, an alkoxy group having 1 to 8 carbon atoms or an alkylthio group having 1 to 8 carbon atoms; X represents a single bond, an oxygen atom, a sulfur atom, a methylene group or a methyleneoxy group (—$CH_2O$—, —$OCH_2$—); q represents an integer of 1 to 5; Y represents a methine group (—CH=) or a nitrogen atom (—N=); provided that the definitions of the above $R^5$, X, Y and q are limited only to the formula (D),

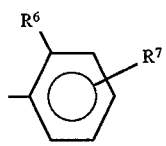

wherein $R^6$ and $R^7$ each represent a hydrogen atom, a halogen atom, an alkyl group having 1 to 3 carbon atoms or an alkoxy group having 1 to 3 carbon atoms; provided that the definitions of the above $R^6$ and $R^7$ are limited only to the formula (E),
is effective as an insecticide and an acaricide.

(10) In Japanese Provisional Patent Publication No. 48907/1994, it has been described that a compound represented by the following formula (F):

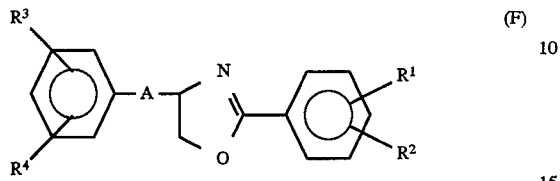

wherein $R^1$ and $R^2$ each represent a halogen atom or the like; $R^3$ and $R^4$ each represent a hydrogen atom, a halogen atom, a trifluoromethyl group, a trifluoromethoxy group, an alkyl group having 1 to 20 carbon atoms, an alkoxy group having 1 to 20 carbon atoms, an alkylthio group having 1 to 20 carbon atoms, a lower alkoxy-lower alkyl group, a lower alkoxy-lower alkoxy group, an alkenyloxy group having 3 or more carbon atoms, a lower alkynyloxy group, a tri(lower alkyl)silyl group, a cycloalkyl group or a group of the formula (G); A represents a direct bond or a lower alkylene group; provided that the definitions of the above $R^1$ to $R^4$ and A are limited only to the formula (F),

wherein B represents a direct bond, an oxygen atom, a lower alkylene group, a lower alkyleneoxy group, a lower alkylenedioxy group or a di(lower alkyl)silyl group; Q represents CH or a nitrogen atom; n represents an integer of 0 to 5; $R^5$ represents a halogen atom, a lower alkyl group, a lower alkoxy group, a lower haloalkyl group, a lower haloalkoxy group or a tri (lower alkyl)silyl group; provided that the definitions of the above B, Q, $R^5$ and n are limited only to the formula (G),
is effective as a chemical for controlling acarines.

However, there has not been disclosed an oxazoline derivative in which 4-position of an oxazoline ring is substituted by a phenoxyalkyl group having a chain of alkylene more than two carbon atoms (i.e., ethylene or higher) as in the present invention.

Thus, the oxazoline derivative of the present invention is a novel compound and it has not been known that the oxazoline derivative of the present invention has an activity of controlling noxious organisms for agriculture and horticulture such as an insecticidal, acaricidal or fungicidal activity.

SUMMARY OF THE INVENTION

An object of the present invention is to provide a novel oxazoline derivative, a process for preparing the same and an agricultural and horticultural chemical for controlling noxious organisms containing said derivative as an active ingredient, which is useful as an insecticide, an acaricide and a fungicide.

The present inventors have studied intensively in order to achieve the above object and consequently found that a novel oxazoline derivative has remarkable controlling activities such as insecticidal, acaricidal and fungicidal activities, which is useful as an agricultural and horticultural chemical for controlling noxious organisms, to accomplish the present invention.

That is, a first invention is concerned with an oxazoline derivative represented by the formula (I):

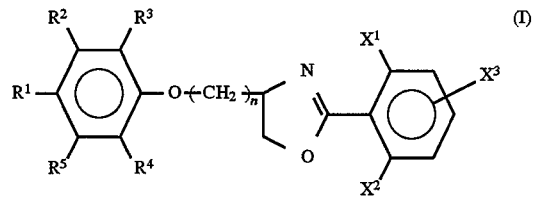

wherein $R^1$ represents a halogen atom; a hydrogen atom; an alkyl group having 1 to 10 carbon atoms; an alkoxy group having 1 to 8 carbon atoms; a haloalkyl group having 1 to 4 carbon atoms; a haloalkoxy group having to 4 carbon atoms; a phenyl group which is unsubstituted or substituted by a halogen atom, a haloalkyl group having 1 to 4 carbon atoms or a haloalkoxy group having 1 to 4 carbon atoms; a phenoxy group which is unsubstituted or substituted by a halogen atom, a haloalkyl group having 1 to 4 carbon atoms or a haloalkoxy group having 1 to 4 carbon atoms; a benzyl group which is unsubstituted or substituted by a halogen atom; a benzyloxy group which is unsubstituted or substituted by a halogen atom; a pyridyloxy group which is unsubstituted or substituted by a haloalkyl group having 1 to 4 carbon atoms or a halogen atom; a pyridylmethyloxy group which is unsubstituted or substituted by a halogen atom; an alkyl group having 1 to 4 carbon atoms substituted by an alkoxy group having 1 to 4 carbon atoms; a nitro group; a cyanomethyloxy group; a haloalkylsulfonyloxy group having 1 to 4 carbon atoms; an alkylsulfonyloxy group having 1 to 4 carbon atoms; or an alkylthio group having 1 to 4 carbon atoms; $R^2$ represents a hydrogen atom, a halogen atom, an alkyl group having 1 to 4 carbon atoms, a haloalkyl group having 1 to 4 carbon atoms, an alkoxy group having 1 to 4 carbon atoms, an alkylthio group having 1 to 4 carbon atoms, or a haloalkoxy group having 1 to 4 carbon atoms; or $R^1$ and $R^2$ may be combined to form a saturated or unsaturated 6-membered ring which ring may contain an oxygen atom and is unsubstituted or substituted by 1 or 2 methyl group; $R^3$ represents a hydrogen atom, a halogen atom or an alkoxy group having 1 to 4 carbon atoms; $R^4$ represents a hydrogen atom, an alkyl group having 1 to 4 carbon atoms, or a halogen atom; $R^5$ represents a hydrogen atom, a halogen atom, or an alkyl group having 1 to 6 carbon atoms; $X^1$ represents a halogen atom, an alkyl group having 1 to 4 carbon atoms, a haloalkyl group having 1 to 4 carbon atoms, or an alkoxy group having 1 to 4 carbon atoms; $X^2$ represents a halogen atom, a hydrogen atom, or an alkoxy group having 1 to 4 carbon atoms; $X^3$ represents a hydrogen atom or a halogen atom; and n represents an integer of 2 to 5.

A second invention is concerned with an amidoethyl halide derivative represented by the formula (II):

$$\underset{R^5}{\underset{|}{R^1}}\underset{R^4}{\overset{R^2}{\bigcirc}}\overset{R^3}{\underset{}{}}-O(CH_2)_{\overline{n}}\overset{NH-CO}{\underset{Y}{\bigcirc}}\overset{X^1}{\underset{X^2}{\bigcirc}}X^3 \quad (II)$$

wherein $R^1$, $R^2$, $R^3$ and n have the same meanings as defined above; and Y represents a halogen atom.

A third invention is concerned with a process for preparing the oxazoline derivative represented by the above formula (I), which comprises cyclizing the amidoethyl halide derivative represented by the above formula (II by treatment with an alkali.

A fourth invention is concerned with an agricultural and horticultural chemical for controlling noxious organisms comprising the oxazoline derivative represented by the above formula (I) as an active ingredient and an insecticidally, acaricidally or fungicidally effective carrier.

DESCRIPTION OF THE PREFERRED EMBODIMENTS

In the following, the present invention is explained in detail.

Desired compound and starting compound

In the oxazoline derivative (compound (I)) represented by the above formula (I) and the starting compound (II), $R^1$ to $R^5$, $X^1$ to $X^3$, n and Y are as described below.

($R^1$)

As $R^1$, there may be mentioned a halogen atom, a hydrogen atom, an alkyl group having 1 to 10 carbon atoms, an alkoxy group having 1 to 8 carbon atoms, a haloalkyl group having 1 to 4 carbon atoms, a haloalkoxy group having 1 to 4 carbon atoms, a phenyl group, a phenoxy group, a benzyl group, a benzyloxy group, a pyridyloxy group, a pyridylmethyloxy group, an alkyl group substituted by an alkoxy group, a nitro group, a cyanomethyloxy group, a haloalkylsulfonyloxy group having 1 to 4 carbon atoms, an alkylsulfonyloxy group, and an alkylthio group having 1 to 4 carbon atoms.

As the halogen atom, there may be mentioned a chlorine atom, an iodine atom, a bromine atom and a fluorine atom, preferably a chlorine atom, a bromine atom and a fluorine atom.

As the alkyl group, there may be mentioned a straight or branched alkyl group having 1 to 10 carbon atoms, preferably those having 1 to 8 carbon atoms, more preferably those having 1 to 6 carbon atoms.

As the alkoxy group, there may be mentioned a straight or branched alkoxy group having 1 to 8 carbon atoms, preferably those having 1 to 6 carbon atoms, more preferably those having 4 to 6 carbon atoms.

As the haloalkyl group, there may be mentioned a straight or branched haloalkyl group having 1 to 4 carbon atoms, preferably those having 1 to 4 carbon atoms and a halogen atom of which is a fluorine atom, more preferably a trifluoromethyl group.

As the haloalkoxy group, there may be mentioned a straight or branched haloalkoxy group having 1 to 4 carbon atoms, preferably a halogen atom of which is a fluorine atom, more preferably a trifluoromethoxy group, a bromodifluoromethoxy group, a 1,1,2,2-tetrafluoroethoxy group, a 2-chloro-1,1,2-trifluoroethoxy group and a 1,1,2,3,3,3-hexafluoropropoxy group.

As the phenyl group, there may be mentioned a phenyl group which is unsubstituted or substituted by a halogen atom, a haloalkyl group having 1 to 4 carbon atoms or a haloalkoxy group having 1 to 4 carbon atoms.

The halogen atom to be used as a substituent for the phenyl group is preferably a chlorine atom; the haloalkyl group is preferably a trifluoromethyl group; and the haloalkoxy group is preferably a trifluoromethoxy group, a difluoromethoxy group and a 2-chloro-1,1,2-trifluoroethoxy group. The position of the substituent on the phenyl group is not particularly limited, and it is preferably 4-position when the substituent is a haloalkyl group or a haloalkoxy group.

As the phenoxy group, there may be mentioned a phenoxy group which is unsubstituted or substituted by a halogen atom, a haloalkyl group having 1 to 4 carbon atoms or a haloalkoxy group having 1 to 4 carbon atoms.

The halogen atom to be used as a substituent for the phenoxy group is preferably a chlorine atom or a fluorine atom; the haloalkyl group is preferably a trifluoromethyl group; and the haloalkoxy group is preferably a trifluoromethoxy group. The position of the substituent on the phenoxy group is not particularly limited, and it is preferably 4-position when the substituent is a haloalkyl group or a haloalkoxy group.

As the benzyl group, there may be mentioned a benzyl group which is unsubstituted or substituted by a halogen atom.

The halogen atom to be used as a substituent for the benzyl group is preferably a chlorine atom. The position of the substituent on the benzyl group is not particularly limited, and it is preferably 4-position.

As the benzyloxy group, there may be mentioned a benzyloxy group which is unsubstituted or substituted by a halogen atom.

The halogen atom to be used as a substituent for the benzyloxy group is preferably a chlorine atom. The position of the substituent on the benzyloxy group is not particularly limited, and it is preferably 4-position.

As the pyridyloxy group, there may be mentioned a pyridyloxy group which is unsubstituted or substituted by a haloalkyl group having 1 to 4 carbon atoms or a halogen atom.

The haloalkyl group to be used as a substituent for the pyridyloxy group is preferably a trifluoromethyl group; and the halogen atom is preferably a chlorine atom. The position of the substituent on the pyridyloxy group is not particularly limited, and in the case of a pyrid-2-yloxy group, it is preferably 5-position when the substituent is a haloalkyl group; and it is preferably 3-position when the substituent is a halogen atom.

As the pyridyloxymethyl group, there may be mentioned a pyridyloxymethyl group which is unsubstituted or substituted by a halogen atom.

The halogen atom is preferably a chlorine atom. The position of the substituent on the pyridyloxy group is not particularly limited, and in the case of a pyrid-3-ylmethyloxy group, it is preferably 6-position.

As the alkyl group substituted by an alkoxy group, there may be mentioned a straight or branched alkyl group substituted by a straight or branched alkoxy group.

As the alkoxy group to be used as a substituent for the alkyl group, there may be mentioned an alkoxy group having 1 to 4 carbon atoms, preferably those having 1 or 2 carbon atoms, more preferably an ethoxy group; and as the substituted alkyl group, there may be mentioned an alkyl group having 1 to 4 carbon atoms, preferably an ethyl group. As the most preferred alkyl group substituted by the alkoxy group, there may be mentioned a 2-ethoxyethyl group.

As the haloalkylsulfonyloxy group, there may be mentioned a straight or branched one, and preferably a trifluoromethylsulfonyloxy group.

As the alkylthio group, there may be mentioned a straight or branched one, and preferably a methylthio group and a n-propylthio group.

($R^2$)

As $R^2$, there may be mentioned a hydrogen atom, a halogen atom, an alkyl group having 1 to 4 carbon atoms, a haloalkyl group having 1 to 4 carbon atoms, an alkoxy group having 1 to 4 carbon atoms, an alkylthio group having 1 to 4 carbon atoms, and a haloalkoxy group having 1 to 4 carbon atoms.

As the halogen atom, there may be mentioned a chlorine atom, an iodine atom, a bromine atom and a fluorine atom, and preferably a chlorine atom and a fluorine atom.

As the alkyl group, there may be mentioned a straight or branched one, and preferably a methyl group.

As the haloalkyl group, there may be mentioned a straight or branched one, and preferably a trifluoromethyl group.

As the alkoxy group, there may be mentioned a straight or branched one, and preferably a methoxy group.

As the alkylthio group, there may be mentioned a straight or branched one, and preferably a propylthio group.

As the haloalkoxy group, there may be mentioned a straight or branched one, and preferably a trifluoromethoxy group.

($R^1$ and $R^2$)

$R^1$ and $R^2$ may be combined to form a saturated or unsaturated 6-membered ring which ring may have an oxygen atom, which ring may be substituted by one or two methyl groups, such as $-OC(CH_3)_2CH_2CH_2-$, $-CH_2CH_2C(CH_3)_2O-$ and $-CH=CH-CH=CH-$.

($R^3$)

As $R^3$, there may be mentioned a hydrogen atom, a halogen atom and an alkoxy group having 1 to 4 carbon atoms.

As the halogen atom, there may be mentioned a chlorine atom, an iodine atom, a bromine atom and a fluorine atom; and preferably a chlorine atom and a fluorine atom.

As the alkoxy group, there may be mentioned a straight or branched one, preferably a methoxy group.

($R^4$)

As $R^4$, there may be mentioned a hydrogen atom, an alkyl group having 1 to 4 carbon atoms and a halogen atom.

As the alkyl group, there may be mentioned a straight or branched one, preferably a methyl group.

As the halogen atom, there may be mentioned a chlorine atom, an iodine atom, a bromine atom and a fluorine atom; and preferably a chlorine atom and a fluorine atom.

($R^5$)

As $R^5$, there may be mentioned a hydrogen atom, a halogen atom and an alkyl group having 1 to 6 carbon atoms.

As the halogen atom, there may be mentioned a chlorine atom, an iodine atom, a bromine atom and a fluorine atom; and preferably a chlorine atom and a fluorine atom.

As the alkyl group, there may be mentioned a straight or branched one, but preferably those having 1 to 4 carbon atoms; more preferably a methyl group and a t-butyl group.

($X^1$)

As $X^1$, there may be mentioned a halogen atom, an alkyl group having 1 to 4 carbon atoms, a haloalkyl group having 1 to 4 carbon atoms, and an alkoxy group having 1 to 4 carbon atoms.

As the halogen atom, there may be mentioned a chlorine atom, an iodine atom, a bromine atom and a fluorine atom, and preferably a chlorine atom, a fluorine atom and a bromine atom.

As the alkyl group, there may be mentioned a straight or branched one, and preferably a methyl group.

As the haloalkyl group, there may be mentioned a straight or branched one, and preferably a trifluoromethyl group.

As the alkoxy group, there may be mentioned a straight or branched one, and preferably a methoxy group.

($X^2$)

As $X^2$, there may be mentioned a halogen atom, a hydrogen atom, and an alkoxy group having 1 to 4 carbon atoms.

As the halogen atom, there may be mentioned a chlorine atom, an iodine atom, a bromine atom and a fluorine atom, and preferably a chlorine atom and a fluorine atom.

As the alkoxy group, there may be mentioned a straight or branched one, and preferably a methoxy group.

($X^3$)

As $X^3$, there may be mentioned a halogen atom, and a hydrogen atom.

As the halogen atom, there may be mentioned a chlorine atom, an iodine atom, a bromine atom and a fluorine atom, and preferably a chlorine atom and a fluorine atom. The position of the substituent on the phenyl group is not particularly limited, and it is preferably 4-position.

(n)

n is an integer of 2 to 5, preferably 2 or 3.

(Y)

Y represents a halogen atom.

As the compound (I), there may be mentioned a compound comprising a combination of various substituents described above. From the point of pharmaceutical effects, the following compounds are preferred:

(1) a compound in which $R^1$, $X^1$ and $X^2$ are halogen atoms, $R^2$ to $R^5$ and $X^3$ are hydrogen atoms, and n is 2;

(2) a compound in which $R^1$ to $R^5$ and $X^3$ are hydrogen atoms, $X^1$ and $X^2$ are halogen atoms, and n is 2;

(3) a compound in which $R^1$ to $R^5$ and $X^3$ are hydrogen atoms, $X^1$ and $X^2$ are halogen atoms, and n is 3;

(4) a compound in which $R^1$, $R^3$, $X^1$ and $X^2$ are halogen atoms, $R^2$, $R^4$, $R^5$ and $X^3$ are hydrogen atoms, and n is 2;

(5) a compound in which $R^1$ is an alkyl group having 1 to 10 carbon atoms, $R^2$ to $R^5$ and $X^3$ are hydrogen atoms, $X^1$ and $X^2$ are halogen atoms, and n is 2;

(6) a compound in which $R^1$ is an alkoxy group having 1 to 8 carbon atoms, $R^2$ to $R^5$ and $X^3$ are hydrogen atoms, $X^1$ and $X^2$ are halogen atoms, and n is 2;

(7) a compound in which $R^1$, $R^2$, $X^1$ and $X^2$ are halogen atoms, $R^3$ to $R^5$ and $X^3$ are hydrogen atoms, and n is 2;

(8) a compound in which $R^1$ is a haloalkyl group having 1 to 4 carbon atoms, $R^2$ to $R^5$ and $X^3$ are hydrogen atoms, $X^1$ and $X^2$ are halogen atoms, and n is 2;

(9) a compound in which $R^1$ is a haloalkoxy group having 1 to 4 carbon atoms, $R^2$ to $R^5$ and $X^3$ are hydrogen atoms, $X^1$ and $X^2$ are halogen atoms, and n is 2;

(10) a compound in which $R^1$ is a phenyl group, $R^2$ to $R^5$ and $X^3$ are hydrogen atoms, $X^1$ and $X^2$ are halogen atoms, and n is 2;

(11) a compound in which $R^1$ is a phenoxy group, $R^2$ to $R^5$ and $X^3$ are hydrogen atoms, $X^1$ and $X^2$ are halogen atoms, and n is 2;

(12) a compound in which $R^1$ is a phenoxy group, $R^2$, $R^5$ and $X^3$ are hydrogen atoms, $R^3$, $X^1$ and $X^2$ are halogen atoms, $R^4$ is an alkyl group having 1 to 8 carbon atoms, and n is 2;

(13) a compound in which $R^1$ is a benzyl group, $R^2$ to $R^5$ and $X^3$ are hydrogen atoms, $X^1$ and $X^2$ are halogen atoms, and n is 2;

(14) a compound in which $R^1$ is an alkyl group having 1 to 4 carbon atoms which is substituted by an alkoxy group having 1 to 4 carbon atoms, $R^2$ to $R^5$ and $X^3$ are hydrogen atoms, $X^1$ and $X^2$ are halogen atoms, and n is

(15) a compound in which $R^1$ is a pyridyloxy group, $R^2$ to $R^5$ and $X^3$ are hydrogen atoms, $X^1$ and $X^2$ are halogen atoms, and n is 2;

(16) a compound in which $R^1$ is a pyridyloxy group, $R^2$, $R^5$, $X^1$ and $X^2$ are halogen atoms, $R^3$, $R^4$ and $X^3$ are hydrogen atoms, and n is 2;

(17) a compound in which $R^1$ is a pyridyloxy group, $R^2$, $X^1$ and $X^2$ are halogen atoms, $R^3$ to $R^5$ and $X^3$ are hydrogen atoms, and n is 2;

(18) a compound in which $R^1$ is a haloalkoxy group having 1 to 4 carbon atoms, $R^2$ to $R^4$ and $X^3$ are hydrogen atoms, $R^5$, $X^1$ and $X^2$ are halogen atoms, and n is 2;

(19) a compound in which $R^1$ is a haloalkoxy group having 1 to 4 carbon atoms, $R^3$ to $R^5$ and $X^3$ are hydrogen atoms, $R^2$, $X^1$ and $X^2$ are halogen atoms, and n is 2;

(20) a compound in which $R^1$ is a haloalkoxy group having 1 to 4 carbon atoms, $R^3$, $R^4$ and $X^3$ are hydrogen atoms, $R^2$, $R^5$, $X^1$ and $X^2$ are halogen atoms, and n is 2;

(21) a compound in which $R^1$, $R^3$, $X^1$ and $X^2$ are halogen atoms, $R^2$, $R^4$, $R^5$ and $X^3$ are hydrogen atoms, and n is

(22) a compound in which $R^1$ is a haloalkyl group having 1 to 4 carbon atoms, $R^2$, $R^4$, $R^5$ and $X^3$ are hydrogen atoms, $R^3$, $X^1$ and $X^2$ are halogen atoms, and n is 2;

(23) a compound in which $R^1$ is a haloalkoxy group having 1 to 4 carbon atoms, $R^2$, $R^4$, $R^5$ and $X^3$ are hydrogen atoms, $R^3$, $X^1$ and $X^2$ are halogen atoms, and n is 2;

(24) a compound in which $R^1$ is a phenoxy group, $R^2$, $R^4$, $R^5$ and $X^3$ are hydrogen atoms, $R^3$, $X^1$ and $X^2$ are halogen atoms, and n is 2;

(25) a compound in which $R^1$ is a n alkyl group having 1 to 10 carbon atoms, $R^2$, $R^4$, $R^5$ and $X^3$ are hydrogen atoms, $R^3$, $X^1$ and $X^2$ are halogen atoms, and n is 2;

(26) a compound in which $R^1$ is a haloalkyl group having 1 to 4 carbon atoms, $R^2$ to $R^5$ and $X^3$ are hydrogen atoms, $X^1$ and $X^2$ are halogen atoms, and n is 3;

(27) a compound in which $R^1$ is a haloalkyl group having 1 to 4 carbon atoms, $R^2$ to $R^5$ and $X^3$ are hydrogen atoms, $X^1$ and $X^2$ are halogen atoms, and n is 5;

(28) a compound in which $R^1$ is a phenyl group, $R^2$ is an alkyl group having 1 to 4 carbon atoms, $R^5$ is an alkyl group having 1 to 4 carbon atoms, $R^3$, $R^4$ and $X^3$ are hydrogen atoms, $X^1$ and $X^2$ are halogen atoms, and n is

(29) a compound in which $R^1$ is a benzyloxy group, $R^2$ to $R^5$ and $X^3$ are hydrogen atoms, $X^1$ and $X^2$ are halogen atoms, and n is 2;

(30) a compound in which $R^1$ is a pyridylmethyloxy group, $R^2$ to $R^5$ and $X^3$ are hydrogen atoms, $X^1$ and $X^2$ are halogen atoms, and n is 2;

(31) a compound in which $R^1$ is a nitro group, $R^2$ to $R^5$ and $X^3$ are hydrogen atoms, $X^1$ and $X^2$ are halogen atoms, and n is 2;

(32) a compound in which $R^1$ is a haloalkylsulfonyloxy group having 1 to 4 carbon atoms, $R^2$ to $R^5$ and $X^3$ are hydrogen atoms, $X^1$ and $X^2$ are halogen atoms, and n is 2;

(33) a compound in which $R^1$, $X^1$ and $X^2$ are halogen atoms, $R^2$ is a haloalkyl group having 1 to 4 carbon atoms, $R^3$ to $R^5$ and $X^3$ are hydrogen atoms, and n is 2;

(34) a compound in which $R^1$, $X^1$ and $X^2$ are halogen atoms, $R^2$, $R^4$, $R^5$ and $X^3$ are hydrogen atoms, $R^3$ is an alkoxy group having 1 to 4 carbon atoms, and n is 2;

(35) a compound in which $R^1$ is an alkylthio group having 1 to 4 carbon atoms, $X^1$ and $X^2$ are halogen atoms, $R^2$ to $R^5$ and $X^3$ are hydrogen atoms, and n is 2;

(36) a compound in which $R^1$, $R^3$ to $R^5$ and $X^3$ are hydrogen atoms, $R^2$ is an alkylthio group having 1 to 4 carbon atoms, $X^1$ and $X^2$ are halogen atoms, and n is 2;

(37) a compound in which $R^1$ and $R^2$ form a saturated 6-membered ring or unsaturated 6-membered ring which ring may have an oxygen atom, which ring may be substituted by one or two methyl groups, $R^3$ to $R^5$ and $X^3$ are hydrogen atoms, $X^1$ and $X^2$ are halogen atoms, and n is 2;

(38) a compound in which $R^1$ to $R^3$, $R^5$, $X^1$ and $X^2$ are halogen atoms, $R^4$ is an alkyl group having 1 to 4 carbon atoms, $X^3$ is a hydrogen atom, and n is 2;

(39) a compound in which $R^1$ is a haloalkoxy group having 1 to 4 carbon atoms, $R^2$, $R^3$, $R^5$, $X^1$ and $X^2$ are halogen atoms, $R^4$ is an alkyl group having 1 to 4 carbon atoms, $X^3$ is a hydrogen atom, and n is 2;

(40) a compound in which $R^1$ is a haloalkoxy group having 1 to 4 carbon atoms, $R^2$ to $R^5$ and $X^3$ are hydrogen atoms, $X^1$ is a haloalkyl group having 1 to 4 carbon atoms, $X^2$ is a halogen atom, and n is 2;

(41) a compound in which $R^1$ is a haloalkoxy group having 1 to 4 carbon atoms, $R^2$ to $R^5$ and $X^2$ are hydrogen atoms, $X^1$ is an alkyl group having 1 to 4 carbon atoms, $X^3$ is a halogen atom, and n is 2;

(42) a compound in which $R^1$ is a haloalkoxy group having 1 to 4 carbon atoms, $R^2$ to $R^5$ are hydrogen atoms, $X^1$ to $X^3$ are halogen atoms, and n is 2;

(43) a compound in which $R^1$ is a haloalkoxy group having 1 to 4 carbon atoms, $R^2$ to $R^5$ and $X^3$ are hydrogen atoms, $X^1$ and $X^2$ are alkoxy groups having 1 to 4 carbon atoms, and n is 2;

(44) a compound in which $R^1$ is a haloalkoxy group having 1 to 4 carbon atoms, $R^2$ to $R^5$ and $X^1$ to $X^3$ are hydrogen atoms, and n is 2; and

(45) a compound in which $R^1$, $R^3$ to $R^5$ and $X^3$ are hydrogen atoms, $R^2$ is a haloalkoxy group having 1 to 4 carbon atoms, $X^1$ and $X^2$ are halogen atoms, and n is 2.

As $R^1$ to $R^5$, $X^1$ to $X^3$, and n in the compounds (I) shown in (1) to (45), there may be mentioned preferred examples and more preferred examples described above.

As these specific compounds (I), there may be mentioned Compounds 1 to 15, 17 to 19, 21 to 27, 31 to 35, 37 to 40, to 44, 49 to 61, 63 to 65, 68 to 73, 75, 77, 79, 82 to 104 and 106 in Table 1 shown below.

The compound (I) can be synthesized by the following method.

Synthesis of the compound (II)

The compound (II) can be synthesized as shown below by reacting the compound (III) with thionyl halide ($SOY_2$) in the presence or absence of a solvent. For the purpose of accelerating the reaction, it is preferred to carry out the reaction under heating.

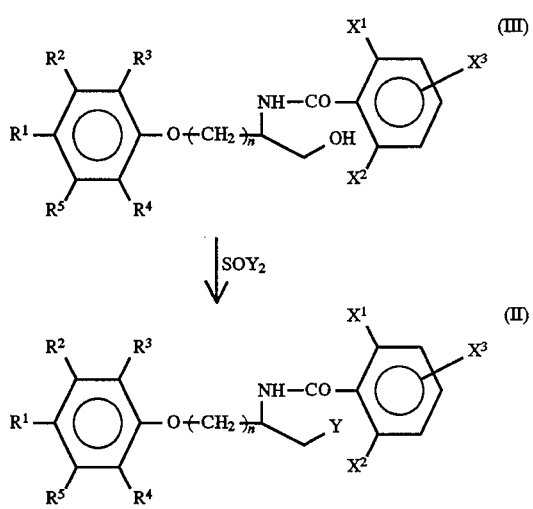

wherein $R^1$ to $R^5$, $X^1$ to $X^3$, n and Y have the same meanings as defined above.

The solvent is not particularly limited so long as it does not participate in the present reaction directly, and may include, for example, chlorinated or unchlorinated aromatic, aliphatic or alicyclic hydrocarbons such as benzene, toluene, xylene, methylnaphthalene, petroleum ether, ligroin, hexane, chlorobenzene, dichlorobenzene, methylene chloride, chloroform, dichloroethane, trichloroethylene and cyclohexane; ethers such as diethyl ether, tetrahydrofuran and dioxane; and a mixture of the above solvents.

The solvent may be used in such an amount that the concentration of the compound (III) becomes 5 to 80% by weight, preferably 10 to 70% by weight.

As the thionyl halide, a commercially available product may be used.

The amount of the thionyl halide to be used is 1 to 5 mole, preferably 1.1 to 2 mole per mole of the compound (III).

The reaction temperature is not particularly limited, but it may be in the temperature range of ice cooling temperature to a boiling point or lower of a solvent used, preferably 50° to 80° C.

The reaction time varies depending on the above concentration and temperature, but it is generally 0.3 to 2 hours.

After completion of the reaction, the compound (II) prepared as described above is subjected to common post-treatments such as extraction, condensation and filtration, and if necessary, it may be purified suitably by a known means such as recrystallization and various chromatographies.

When the compound (II) is used as a synthetic starting material of the compound (I), the compound (II) can be used as such without post-treatments after the above synthetic reaction.

As the compound (II), there may be mentioned compounds comprising the respective substituents corresponding to the respective compounds shown in Table 1 (the compounds (2) comprising the respective substituents corresponding to Compounds 1 to 106 are referred to as Compound $(II)_1$ to Compound $(II)_{106}$ and, for example, Compound $(II)_1$ comprising the respective substituents corresponding to Compound 1 is a compound in which $R^1$ is a chlorine atom, $R^2$ to $R^5$ and $X^3$ are hydrogen atoms, $X^1$ and $X^3$ are fluorine atoms, n is 2 and Y is a halogen atom).

Synthetic method of the compound (I)

The compound (I) can be synthesized generally by cyclizing the starting compound (II) by treatment with an alkali in the presence or absence of a solvent. For the purpose of accelerating the reaction, it is preferred to carry out the reaction under heating.

The solvent is not particularly limited so long as it does not participate in the present reaction directly, and may include, for example, chlorinated or unchlorinated aromatic, aliphatic or alicyclic hydrocarbons such as benzene, toluene, xylene, methylnaphthalene, petroleum ether, ligroin, hexane, chlorobenzene, dichlorobenzene, methylene chloride, chloroform, dichloroethane, trichloroethylene and cyclohexane; ethers such as diethyl ether, tetrahydrofuran and dioxane; alcohols such as methanol, ethanol, propanol and butanol; and a mixture of the above solvents. Preferred are ethers and alcohols.

The solvent may be used in such an amount that the concentration of the compound (II) becomes 5 to 80% by weight, preferably 10 to 70% by weight.

The kind of the alkali is not particularly limited, and may include, for example, an inorganic base such as sodium hydroxide, potassium hydroxide, sodium carbonate, potassium carbonate and sodium hydrogen carbonate, preferably sodium hydroxide and potassium hydroxide.

The amount of the alkali to be used is 1 to 10 mole, preferably 2 to 5 mole per mole of the compound (II).

The reaction temperature is not particularly limited, but it may be in the temperature range of ice cooling temperature to a boiling point or lower of a solvent used, preferably 50° to 80° C.

The reaction time varies depending on the above concentration and temperature, but it is generally 0.3 to 2 hours.

After completion of the reaction, the compound (I) prepared as described above is subjected to common post-treatments such as extraction, condensation and filtration, and if necessary, it may be purified suitably by a known means such as recrystallization and various chromatographies.

As the compound (i), there may be mentioned Compounds 1 to 32 shown in Table 1 (Compound 1 is a compound represented by the formula (I) in which $R^1$ is a chlorine atom, $R^2$ to $R^5$ and $X^3$ are hydrogen atoms, $X^1$ and $X^3$ are fluorine atoms, and n is 2).

Agricultural and horticultural chemical for Controlling noxious organisms (Controlling effect)

As the agricultural and horticultural noxious organisms on which a controlling effect by the compound (I) of the present invention can be observed, there may be mentioned agricultural and horticultural noxious insects (e.g. Hemiptera (planthoppers, leafhoppers, aphides and white-flies), Lepidoptera (cabbage armyworms, diamond-back moth, leafroller moths, pyralid moths and common cabbage worm), Coleoptera (Tenebrionid beetles, leafbeetles, weevils and scarabs) and Acarina (citrus red mite and two-spotted spider mite of Tetranychidae family and pink citrus rust mite of Eriophyidae family)), hygienically noxious insects (e.g. flies, mosquitoes and cockroaches), noxious insects of stored grains (rust-red flour beetles and bean weevils), and root knot nematode, pine wood nematode and bulb mite in soil, and also agricultural and horticultural diseases (e.g. brown rust (wheat), powdery mildew (barley), downy mildew (cucumber), blast (rice) and late blight (tomato)).

(Chemical for controlling noxious organisms)

The agricultural and horticultural chemical for controlling noxious organisms of the present invention has remarkable insecticidal, acaricidal and fungicidal effects, and contains at least one compound (I) as an active ingredient.

The compound (I) can be used singly, but may be preferably used by mixing with a carrier, a surfactant, a dispersant and an auxiliary (for example, prepared as a composition such as a dustable powder, an emulsifiable concentrate, a fine granule, a granule, a wettable powder, an oily suspension and an aerosol) according to a conventional method.

As the carrier, any insecticidally, acaricidally or fungicidally effective carrier may be used with an insecticidally, acaricidally or fungicidally effective amount, and there may be mentioned, for example, a solid carrier such as talc, bentonite, clay, kaolin, diatomaceous earth, white carbon, vermiculite, calcium hydroxide, siliceous sand, ammonium sulfate and urea; a liquid carrier such as hydrocarbons (e.g. kerosine and mineral oil), aromatic hydrocarbons (e.g. benzene, toluene and xylene), chlorinated hydrocarbons (e.g. chloroform and carbon tetrachloride), ethers (e.g. dioxane and tetrahydrofuran), ketones (e.g. acetone, cyclohexanone and isophorone), esters (e.g. ethyl acetate, ethylene glycol acetate and dibutyl maleate), alcohols (e.g. methanol, n-hexanol and ethylene glycol), polar solvents (e.g. dimethylformamide and dimethyl sulfoxide) and water; and a gas carrier such as air, nitrogen, carbon dioxide and freon (trade name, produced by Du Pont de Nemours & Co. Inc.) (in the case of a gas carrier, mixed spray can be carried out).

As the surfactant and dispersant which can be used for improving attachment of the present chemical to and absorption thereof in animals and plants, and improving characteristics such as dispersion, emulsification and spreading of the chemical, there may be mentioned, for example, alcohol sulfates, alkylsulfonate, lignosulfonate and polyoxyethylene glycol ether. Further, for improving properties of its formulation, for example, carboxymethyl cellulose, polyethylene glycol and gum arabic can be used as an auxiliary.

In preparation of the present chemical, the above carrier, surfactant, dispersant and auxiliary can be used singly or in a suitable combination, respectively, depending on the respective purposes.

When the compound (I) of the present invention is made into formulations, the concentration of the active ingredient is generally 1 to 50% by weight in an emulsifiable concentrate, generally 0.3 to 25% by weight in a dustable powder, generally 1 to 90% by weight in a wettable powder, generally 0.5 to 5% by weight in a granule, generally 0.5 to 5% by weight in an oily suspension, and generally 0.1 to 5% by weight in an aerosol.

These formulations can be provided for various uses by diluting them to have a suitable concentration and spraying them to stems and leaves of plants, soil and paddy field surface, or by applying them directly thereto, depending on the purposes.

EXAMPLES

The present invention is described in detail by referring to Examples, but the scope of the present invention is not limited by these Examples.

Example 1

(Syntheses of the compounds (2))

(1) Synthesis of N-[3-(4-bromophenoxy)-1-chloromethyl-propyl]-2,6-difluorobenzamide In 20 ml of toluene was dissolved 4.80 g of N-[3-(4-bromophenoxy)-1-hydroxymethylpropyl]-2,6-difluorobenzamide, and 2.9 g of thionyl chloride was added to the solution. The mixture was stirred at 70° to 80° C. for 1 hour.

After cooling, an excessive amount of thionyl chloride and the solvent were removed under reduced pressure. The resulting oily product was isolated by silica gel column chromatography (Wako gel C-200 (trade name, manufactured by Wako Junyaku Co.), eluted by toluene:ethyl acetate=9:1) to obtain 4.55 g of the title compound as white crystals.

m.p.: 116° to 119° C.

(2) Synthesis of N-[3-(4-methylphenoxy)-1-chloromethylpropyl]-2, 6-difluorobenzamide In 20 ml of toluene was dissolved 4.02 g of N-[3-(4-methyl-phenoxy)-1-hydroxymethylpropyl]-2,6-difluorobenzamide, and 2.9 g of thionyl chloride was added to the solution. The mixture was stirred at 70° to 80° C. for 1 hour.

After cooling, an excessive amount of thionyl chloride and the solvent were removed under reduced pressure. The resulting oily product was isolated by silica gel column chromatography (Wako gel C-200 (trade name, manufactured by 5 Wako Junyaku Co.), eluted by toluene:ethyl acetate=9:1) to obtain 3.91 g of the title compound as white crystals.

m.p.: 97° to 99° C.

(3) Syntheses of other compounds (2) in Table 1

According to the methods described in the above (1) and (2), the other compounds (2) shown in Table 1 were synthesized.

Example 2

(Syntheses of the compounds (1))

(1) Synthesis of 2-(2,6-difluorophenyl)-4-[2-(4-chlorophenoxy)ethyl]-2-oxazoline (Compound 1)

In 20 ml of methanol was dissolved 3.74 g of N-[3-(4-chlorophenoxy)-1-chloromethylpropyl]-2,6-difluorobenzamide, and 5 ml of a 15% sodium hydroxide aqueous solution was added to the solution. The mixture was refluxed under heating for 1 hour.

After completion of the reaction, the solvent was removed under reduced pressure. The reaction mixture was extracted with ethyl acetate, washed with a saturated saline solution and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene-:ethyl acetate=9:1) to obtain 2.42 g of the title compound as a colorless oily product.

$^1$H-NMR (CDCl$_3$, δ ppm) 2.04 to 2.30 (2H, m), 4.16 (2H, t, J=6 Hz), 4.19 to 4.33 ($^1$H, m), 4.37 to 4.69 (2H, m), 6.79 to 7.46 (7H, m)

(2) Synthesis of 2-(2,6-difluorophenyl)-4-[2-(4-bromophenoxy) ethyl]-2-oxazoline (Compound 2)

In 20 ml of methanol was dissolved 4.19 g of N-[3-(4-bromophenoxy)-1-chloromethylpropyl]-2,6-difluorobenzamide, and 5 ml of a 15% sodium hydroxide aqueous solution was added to the solution. The mixture was refluxed under heating for 1 hour.

After completion of the reaction, the solvent was removed under reduced pressure. The reaction mixture was extracted with ethyl acetate, washed with a saturated saline solution and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene-:ethyl acetate=9:1) to obtain 3.06 g of the title compound as a colorless oily product.

$^1$H-NMR (CDCl$_3$, δ ppm) 2.02 to 2.29 (2H, m), 4.16 (2H, t, J=6 Hz), 4.19 to 4.30 ($^1$H, m), 4.38 to 4.68 (2H, m), 6.73 to 7.46 (7H, m)

(3) Synthesis of 2-(2,6-difluorophenyl)-4-(3-phenoxypropyl-2-oxazoline (Compound 4)

In 20 ml of methanol was dissolved 3.54 g of N-(1-chloromethyl-4-phenoxybutyl)-2,6-difluorobenzamide, and 5 ml of a 15% sodium hydroxide aqueous solution was added to the solution. The mixture was refluxed under heating for 1 hour.

After completion of the reaction, the solvent was removed under reduced pressure. The reaction mixture was extracted with ethyl acetate, washed with a saturated saline solution and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene : ethyl acetate=9:1) to obtain 1.74 g of the title compound as a colorless oily product.

$^1$H-NMR (CDCl$_3$, δ ppm) 1.72 to 2.13 (4H, m), 3.89 to 4.08 ($^1$H, m), 4.12 (2H, t, J=7 Hz), 4.34 to 4.58 (2H, m), 6.78 to 7.44 (8H, m)

(4) Synthesis of 2-(2, 6-difluorophenyl)-4-[2-(4-phenoxyphenoxy)ethyl]-2-oxazoline (Compound 13)

In 20 ml of methanol was dissolved 3.02 g of N-[1-chloromethyl-3-(4-phenoxyphenoxy)-propyl]-2,6-difluorobenzamide, and 3.5 ml of a 15% sodium hydroxide aqueous solution was added to the solution. The mixture was refluxed under heating for 1 hour.

After completion of the reaction, the solvent was removed under reduced pressure. The reaction mixture was extracted with ethyl acetate, washed with a saturated saline solution and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene- :ethyl acetate=20:1) to obtain 1.97 g of the title compound as a pale yellow oily product.

$^1$H-NMR (CDCl$_3$, δ ppm) 2.04 to 2.35 (2H, m), 4.17 (2H, t, J=3.5 Hz), 4.22 to 4.30 ($^1$H, m), 4.50 to 4.68 (2H, m), 6.70 to 7.46 (12H, m)

(5) Synthesis of 2-(2,6-difluorophenyl)-4-{2-[4-(2-ethoxyethyl)phenoxy]ethyl}-2-oxazoline (Compound 17)

In 20 ml of methanol was dissolved 2.06 g of N-{1-chloromethyl-3-[4-(ethoxyethyl)phenoxy]-propyl}-2,6-difluorobenzamide, and 2.5 ml of a 15% sodium hydroxide aqueous solution was added to the solution. The mixture was refluxed under heating for 1 hour.

After completion of the reaction, the solvent was removed under reduced pressure. The reaction mixture was extracted with ethyl acetate, washed with a saturated saline solution and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene- :ethyl acetate=9:1) to obtain 1.14 g of the title compound as a colorless oily product.

$^1$H-NMR (CDCl$_3$, δ ppm) 1.20 (3H, t, J=7 Hz), 2.02 to 2.31 (2H, m), 2.83 (2H, t, J=7 Hz), 3.50 (2H, q, J=7 Hz), 3.59 (2H, t, J=7 Hz), 4.16 (2H, t, J=3.5 Hz), 4.20 to 4.31 ($^1$H, m), 4.47 to 4.63 (2H, m), 6.75 to 7.44 (7H, m)

(6) Synthesis of 2-(2,6-difluorophenyl)-4-{2-[4-(3-chloro-5-trifluoromethylpyridin-2-yloxy) phenoxy]ethyl }-2-oxazoline (Compound 19)

In 20 ml of methanol was dissolved 2.68 g of N-{1-chloromethyl-3-[4-(3-chloro-5-trifluoromethylpyrido-2-yloxy)phenoxy-propyl]}-2,6-difluorobenzamide, and 2.5 ml of a 15% sodium hydroxide aqueous solution was added to the solution. The mixture was refluxed under heating for 1 hour.

After completion of the reaction, the solvent was removed under reduced pressure. The reaction mixture was extracted with ethyl acetate, washed with a saturated saline solution and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene : ethyl acetate=20:1) to obtain 1.09 g of the title compound as a colorless viscous oily product.

$^1$H-NMR (CDCl$_3$, δ ppm) 2.03 to 2.32 (2H, m), 4.14 to 4.31 (3H, m), 4.50 to 4.63 (2H, m), 6.78 to 7.45 (7H, m), 7.97 ($^1$H, s), 8.28 ($^1$H, s)

(7) Synthesis of 2-(2, 6-difluorophenyl)-4-[2-(4-trifluoromethoxyphenoxy)ethyl]-2-oxazoline (Compound 11)

In 20 ml of methanol was dissolved 1.27 g of N-[1-chloromethyl- 3-(4-trifluoromethoxyphenoxy)propyl]-2,6-difluorobenzamide, and 1.5 ml of a 15% sodium hydroxide aqueous solution was added to the solution. The mixture was refluxed under heating for 1 hour.

After completion of the reaction, the solvent was removed under reduced pressure. The reaction mixture was extracted with ethyl acetate, washed with a saturated saline solution and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene : ethyl acetate=9:1) to obtain 0.87 g of the title compound as colorless crystals.

$^1$H-NMR (CDCl$_3$, δ ppm) 2.07 to 2.29 (2H, m), 4.06 to 4.38 (3H, m), 4.47 to 4.70 (2H, m), 6.78 to 7.46 (7H, m)

(8) Synthesis of 2-(2,6-difluorophenyl)-4-[2-(4-chlorophenoxyphenoxy) ethyl]-2-oxazoline (Compound 21)

In 20 ml of methanol was dissolved 1.40 g of N-[1-chloromethyl-3-(4-chlorophenoxyphenoxy)propyl]-2,6-difluorobenzamide, and 1.5 ml of a 15% sodium hydroxide aqueous solution was added to the solution. The mixture was refluxed under heating for 1 hour.

After completion of the reaction, the solvent was removed under reduced pressure. The reaction mixture was extracted with ethyl acetate, washed with a saturated saline solution and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene : ethyl acetate=9:1) to obtain 0.98 g of the title compound as a pale yellow oily product.

$^1$H-NMR (CDCl$_3$, δ ppm) 2.11 to 2.30 (2H, m), 4.14 to 4.30 (3H, m), 4.55 to 4.65 (2H, m), 6.80 to 7.45 (11H, m)

(9) Synthesis of 2-(2,6-difluorophenyl)-4-{2-[4-(1, 1,2,3, 3,3-hexafluoro-1-propoxy) phenoxy]ethyl}-2-oxazoline (Compound 43)

In 20 ml of methanol was dissolved 1.52 g of N-{1-chloromethyl-3-[4-(1,1,2,3,3,3-hexafluoro-1-propoxy) Phenoxy]-propyl}-2,6-difluorobenzamide, and 1.5 ml of a 15% sodium hydroxide aqueous solution was added to the solution. The mixture was refluxed under heating for 1 hour.

After completion of the reaction, the solvent was removed under reduced pressure. The reaction mixture was extracted with ethyl acetate, washed with a saturated saline solution and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene-:ethyl acetate=9:1) to obtain 1.02 g of the title compound as a pale yellow viscous oily product.

$^1$H-NMR (CDCl$_3$, δ ppm) 1.97° to 2.31 (2H, m), 4.05 to 4.30 (3H, m), 4.43 to 4.67 (2H, m), 4.80 to 5.12 ($^1$H, m), 6.68 to 7.52 (7H, m)

(10) Synthesis of 2-(2, 6-difluorophenyl)-4-{2-[4-(4-trifluoromethylphenyl) phenoxy]ethyl }-2-oxazoline (Compound 63)

In 15 ml of methanol was dissolved 0.97 g of N-{1-chloromethyl-3-[4-trifluoromethylphenyl)phenoxy] Propyl}-2,6-difluorobenzamide, and 1.0 ml of a 15% sodium hydroxide aqueous solution was added to the solution. The mixture was refluxed under heating for 1 hour.

After completion of the reaction, the solvent was removed under reduced pressure. The reaction mixture was extracted with ethyl acetate, washed with a saturated saline solution and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene-:ethyl acetate=9:1) to obtain 0.59 g of the title compound as colorless crystals.

$^1$H-NMR (CDCl$_3$, δ ppm) 2.08 to 2.35 (2H, m), 4.10 to 4.38 (3H, m), 4.47 to 4.71 (2H, m), 6.78 to 7.78 (11H, m)

(11) Synthesis of 2-(2,6-difluorophenyl)-4-{2-[4-(4-trifluoromethoxyphenyl)phenoxy]ethyl}-2-oxazoline (Compound 65)

In 15 ml of methanol was dissolved 1.00 g of N-{1-chloromethyl-3-[4-trifluoromethylphenyl)Phenoxy] Propyl}-2,6-difluorobenzamide, and 1.0 ml of a 15% sodium hydroxide aqueous solution was added to the solution. The mixture was refluxed under heating for 1 hour.

After completion of the reaction, the solvent was removed under reduced pressure. The reaction mixture was extracted with ethyl acetate, washed with a saturated saline solution and dried over anhydrous sodium sulfate. Then, the solvent was removed under reduced pressure.

The resulting oily product was isolated by silica gel column chromatography (Wako gel C-200 (trade name, manufactured by Wako junyaku Co.), eluted by toluene-:ethyl acetate=9:1) to obtain 0.54 g of the title compound as colorless crystals.

$^1$H-NMR (CDCl$_3$, δ ppm) 2.03 to 2.35 (2H, m), 4.05 to 4.34 (3H, m), 4.48 to 4.72 (2H, m), 6.78 to 7.69 (11H, m)

(12) Synthesis of 2-(2,6-difluorophenyl)-4-[2-(2,2-dimethyl-3, 4-dihydro-2H-chromen-6-yloxy) ethyl]-2-oxazoline (Compound 85)

In 20 ml of methanol was dissolved 1.27 g of N-[1-chloromethyl-3-(2,2-dimethyl-3,4-dihydro-2H-chromen-6-yloxy)propyl]-2,6-difluorobenzamide, and 1.5 ml of a 15% sodium hydroxide aqueous solution was added to the solution. The mixture was refluxed under heating for 1 hour.

After completion of the reaction, the solvent was removed under reduced pressure. The reaction mixture was extracted with ethyl acetate, washed with a saturated saline solution and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene-:ethyl acetate=9:1) to obtain 0.77 g of the title compound as a pale yellow viscous oily product.

$^1$H-NMR (CDCl$_3$, δ ppm) 1.31 (6H, s), 1.77 (2H, t, J=7.3 Hz), 2.02 to 2.32 (2H, m), 2.74 (2H, t, J=6.7 Hz), 4.02 to 4.30 (3H, m), 4.48 to 4.63 (2H, m), 6.58 to 7.47 (6H, m)

(13) Synthesis of 2-(2-chloro-6-fluorophenyl)-4-[2-(4-trifluoromethoxyphenoxy) ethyl]-2-oxazoline (Compound 98)

In 20 ml of methanol was dissolved 1.32 g of N-[1-chloromethyl-3-(4-trifluoromethoxyphenoxy)propyl]-2-chloro-6-fluorobenzamide, and 1.5 ml of a 15% sodium hydroxide aqueous solution was added to the solution. The mixture was refluxed under heating for 1 hour.

After completion of the reaction, the solvent was removed under reduced pressure. The reaction mixture was extracted with ethyl acetate, washed with a saturated saline solution and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene-:ethyl acetate=9:1) to obtain 0.83 g of the title compound as a colorless oily product.

$^1$H-NMR (CDCl$_3$, δ ppm)
2.18 to 2.25 (2H, m), 4.17 to 4.29 (3H, m), 4.57 to 4.68 (2H, m), 6.86 to 7.38 (7H, m)

(14) Synthesis of 2-(2,6-dichlorophenyl)-4-[2-(4-trifluoromethoxyphenoxy) ethyl]-2-oxazoline (Compound 99)

In 20 ml of methanol was dissolved 1.37 g of N-[1-chloromethyl-3-(4-trifluoromethoxyphenoxy)propyl]-2,6-dichlorobenzamide, and 1.5 ml of a 15% sodium hydroxide aqueous solution was added to the solution. The mixture was refluxed under heating for 1 hour.

After completion of the reaction, the solvent was removed under reduced pressure. The reaction mixture was extracted with ethyl acetate, washed with a saturated saline solution and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene : ethyl acetate=9:1) to obtain 0.94 g of the title compound as a pale yellow viscous oily product.

$^1$H-NMR (CDCl$_3$, δ ppm)
2.07 to 2.29 (2H, m), 4.06 to 4.38 (3H, m), 4.47 to 4.70 (2H, m), 6.78 to 7.43 (7H, m)

(15) Synthesis of 2-(2, 6-difluorophenyl)-4-[2-(2-naphthyloxy) ethyl]-2-oxazoline (Compound 105)

In 20 ml of methanol was dissolved 1.32 g of N-[1-chloromethyl-3-(2-naphthyloxy)propyl]-2,6-difluorobenzamide, and 1.5 ml of a 15% sodium hydroxide aqueous solution was added to the solution. The mixture was refluxed under heating for 1 hour.

After completion of the reaction, the solvent was removed under reduced pressure. The reaction mixture was extracted with ethyl acetate, washed with a saturated saline solution and dried over anhydrous sodium sulfate. Then, the solvent was removed under reduced pressure.

The resulting oily product was isolated by silica gel column chromatography (Wako gel C-200 (trade name, manufactured by Wako Junyaku Co.), eluted by toluene-:ethyl acetate=9:1) to obtain 0.87 g of the title compound as a pale yellow oily product.

$^1$H-NMR (CDCl$_3$, δ ppm) 2.10 to 2.39 (2H, m), 4.14 to 4.39 (3H, m), 4.47 to 4.70 (2H, m), 6.82 to 7.80 (10H, m)

(16) Syntheses of other compounds (I) in Table 1

According to the methods described in the above (1) to (15), the other compounds (I) shown in Table 1 were synthesized.

The compounds thus synthesized are shown in Table 1.

TABLE 1

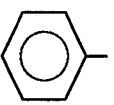
(I)

| Compound | R¹ | R² | R³ | R⁴ | R⁵ | X¹ | X² | X³ | n | Physical property |
|---|---|---|---|---|---|---|---|---|---|---|
| 1 | Cl | H | H | H | H | F | F | H | 2 | $n_D^{22.7}$ 1.5557 |
| 2 | Br | H | H | H | H | F | F | H | 2 | $n_D^{23.1}$ 1.5644 |
| 3 | H | H | H | H | H | F | F | H | 2 | $n_D^{23.1}$ 1.5505 |
| 4 | H | H | H | H | H | F | F | H | 3 | $n_D^{19.8}$ 1.5466 |
| 5 | H | H | Cl | H | H | F | F | H | 2 | $n_D^{23.0}$ 1.5591 |
| 6 | CH₃ | H | H | H | H | F | F | H | 2 | $n_D^{20.8}$ 1.5448 |
| 7 | CH₃O— | H | H | H | H | F | F | H | 2 | $n_D^{21.0}$ 1.5487 |
| 8 | Cl | Cl | H | H | H | F | F | H | 2 | $n_D^{21.0}$ 1.5292 |
| 9 | t-C₄H₉ | H | H | H | H | F | F | H | 2 | m.p. 73~75° C. |
| 10 | CF₃ | H | H | H | H | F | F | H | 2 | m.p. 68~70° C. |
| 11 | CF₃O— | H | H | H | H | F | F | H | 2 | m.p. 48~50° C. |
| 12 | 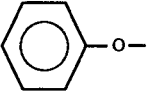 | H | H | H | H | F | F | H | 2 | m.p. 67~69° C. |
| 13 | 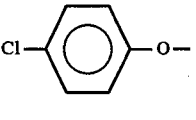 | H | H | H | H | F | F | H | 2 | $n_D^{23.9}$ 1.5760 |
| 14 | 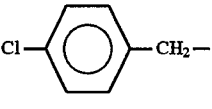 | H | Cl | CH₃ | H | F | F | H | 2 | $n_D^{23.1}$ 1.5664 |
| 15 | 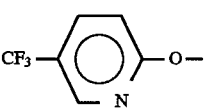 | H | Cl | CH₃ | H | F | F | H | 2 | $n_D^{21.1}$ 1.5842 |
| 16 | CH₃OCH₂CH₂— | H | H | H | H | F | F | H | 2 | |
| 17 | C₂H₅OCH₂CH₂— | H | H | H | H | F | F | H | 2 | $n_D^{21.0}$ 1.5662 |
| 18 | 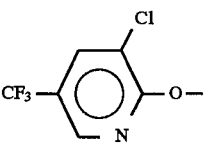 | H | H | H | H | F | F | H | 2 | $n_D^{21.1}$ 1.5446 |
| 19 | 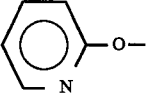 | H | H | H | H | F | F | H | 2 | Shown in Table 2 |
| 20 | 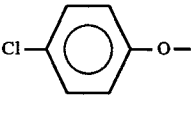 | H | H | H | H | F | F | H | 2 | |
| 21 | 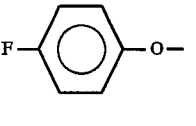 | H | H | H | H | F | F | H | 2 | $n_D^{21.0}$ 1.5757 |
| 22 |  | H | H | H | H | F | F | H | 2 | $n_D^{20.0}$ 1.5706 |

TABLE 1-continued (I)

| Compound | R¹ | R² | R³ | R⁴ | R⁵ | X¹ | X² | X³ | n | Physical property |
|---|---|---|---|---|---|---|---|---|---|---|
| 23 | 4-CF₃-C₆H₄-O— | H | H | H | H | F | F | H | 2 | $n_D^{20.0}$ 1.5449 |
| 24 | 3-Cl-4-CF₃-C₆H₃-O— | H | H | H | H | F | F | H | 2 | $n_D^{20.0}$ 1.5477 |
| 25 | F | H | F | H | H | F | F | H | 2 | m.p. 70~72° C. |
| 26 | 4-CF₃O-C₆H₄-O— | H | H | H | H | F | F | H | 2 | $n_D^{19.8}$ 1.5374 |
| 27 | n-C₄H₉O— | H | H | H | H | F | F | H | 2 | $n_D^{19.0}$ 1.5363 |
| 28 | H | H | H | H | H | F | F | H | 4 | |
| 29 | " | H | H | H | H | F | F | H | 5 | |
| 30 | Cl | H | H | H | H | F | F | H | 5 | |
| 31 | 3-Cl-4-CF₃-2-pyridyl-O— | Cl | H | H | Cl | F | F | H | 2 | m.p. 86~88° C. |
| 32 | n-C₆H₁₃ | H | H | H | H | F | F | H | 2 | $n_D^{17.2}$ 1.5306 |
| 33 | 3-Cl-5-CF₃-2-pyridyl-O— | Cl | H | H | H | F | F | H | 2 | Shown in Table 2 |
| 34 | n-C₆H₁₃O— | H | H | H | H | F | F | H | 2 | $n_D^{20.3}$ 1.5302 |
| 35 | CHF₂O— | H | H | H | H | F | F | H | 2 | $n_D^{20.0}$ 1.5253 |
| 36 | CClF₂O— | H | H | H | H | F | F | H | 2 | |
| 37 | CBrF₂O— | H | H | H | H | F | F | H | 2 | $n_D^{20.1}$ 1.5317 |
| 38 | CHF₂CHFO— | H | H | H | H | F | F | H | 2 | $n_D^{19.8}$ 1.5198 |
| 39 | CHF₂CF₂O— | H | H | H | H | F | F | H | 2 | $n_D^{20.0}$ 1.5008 |
| 40 | CF₃CH₂O— | H | H | H | H | F | F | H | 2 | m.p. 50~52° C. |
| 41 | CF₃CF₂O— | H | H | H | Cl | F | F | H | 2 | |
| 42 | CHClFCF₂O— | H | H | H | H | F | F | H | 2 | m.p. 71~74° C. |
| 43 | CF₃CHFCF₂O— | H | H | H | H | F | F | H | 2 | Shown in Table 2 |
| 44 | CHF₂O— | Cl | H | H | Cl | F | F | H | 2 | m.p. 52~54° C. |
| 45 | CClF₂O— | Cl | H | H | Cl | F | F | H | 2 | |
| 46 | CBrF₂O— | Cl | H | H | Cl | F | F | H | 2 | |
| 47 | CF₃O— | Cl | H | H | Cl | F | F | H | 2 | |
| 48 | CHF₂CF₂O— | Cl | H | H | Cl | F | F | H | 2 | |
| 49 | CHClFCF₂O— | Cl | H | H | Cl | F | F | H | 2 | m.p. 66~68° C. |
| 50 | F | H | H | H | H | F | F | H | 2 | $n_D^{19.9}$ 1.5364 |
| 51 | I | H | H | H | H | F | F | H | 2 | $n_D^{19.9}$ 1.5978 |
| 52 | Cl | H | Cl | H | H | F | F | H | 2 | m.p. 66~67° C. |
| 53 | Br | H | F | H | H | F | F | H | 2 | $n_D^{20.0}$ 1.5599 |
| 54 | CF₃ | H | Cl | H | H | F | F | H | 2 | m.p. 95~97° C. |
| 55 | CF₃O— | H | Cl | H | H | F | F | H | 2 | $n_D^{19.9}$ 1.5152 |

TABLE 1-continued $$\text{R}^1\text{-}\text{C}_6\text{H}_2(\text{R}^2)(\text{R}^3)(\text{R}^4)(\text{R}^5)\text{-O-(CH}_2)_n\text{-[oxazoline]-C}_6\text{H}_2(\text{X}^1)(\text{X}^2)(\text{X}^3)$$  (I)

| Compound | R¹ | R² | R³ | R⁴ | R⁵ | X¹ | X² | X³ | n | Physical property |
|---|---|---|---|---|---|---|---|---|---|---|
| 56 | C₆H₅-O- | H | Cl | H | H | F | F | H | 2 | $n_D^{20.0}$ 1.5826 |
| 57 | Cl-C₆H₄-O- | H | Cl | H | H | F | F | H | 2 | $n_D^{20.0}$ 1.5952 |
| 58 | t-C₄H₉ | H | Cl | H | H | F | F | H | 2 | m.p. 76~78° C. |
| 59 | C₆F₅-O- | H | H | H | H | F | F | H | 2 | m.p. 70~73° C. |
| 60 | CF₃ | H | H | H | H | F | F | H | 3 | $n_D^{20.0}$ 1.5118 |
| 61 | CF₃ | H | H | H | H | F | F | H | 5 | $n_D^{20.0}$ 1.5094 |
| 62 | Cl-C₆H₄- | H | H | H | H | F | F | H | 2 |  |
| 63 | CF₃-C₆H₄- | H | H | H | H | F | F | H | 2 | m.p. 96–99° C. |
| 64 | CHF₂O-C₆H₄- | H | H | H | H | F | F | H | 2 | m.p. 93~96° C. |
| 65 | CF₃O-C₆H₄- | H | H | H | H | F | F | H | 2 | m.p. 71~74° C. |
| 66 | CClF₂O-C₆H₄- | H | H | H | H | F | F | H | 2 |  |
| 67 | CBrF₂O-C₆H₄- | H | H | H | H | F | F | H | 2 |  |
| 68 | CHClFCF₂O-C₆H₄- | H | H | H | H | F | F | H | 2 | m.p. 93~95° C. |
| 69 | Cl-C₆H₄- | CH₃ | H | H | CH₃ | F | F | H | 2 | $n_D^{20.0}$ 1.5811 |

TABLE 1-continued (I)

[Structure: R¹, R², R³, R⁴, R⁵ substituted phenyl—O—(CH₂)ₙ—N(C=O)—phenyl with X¹, X², X³]

| Compound | R¹ | R² | R³ | R⁴ | R⁵ | X¹ | X² | X³ | n | Physical property |
|---|---|---|---|---|---|---|---|---|---|---|
| 70 | phenyl-CH₂O— | H | H | H | H | F | F | H | 2 | m.p. 109~110° C. |
| 71 | Cl-phenyl-CH₂O— | H | H | H | H | F | F | H | 2 | m.p. 92~94° C. |
| 72 | Cl-pyridyl-CH₂O— | H | H | H | H | F | F | H | 2 | m.p. 87~88° C. |
| 73 | NO₂ | H | H | H | H | F | F | H | 2 | m.p. 95~97° C. |
| 74 | NCCH₂O— | H | H | H | H | F | F | H | 2 | m.p. 81~83° C. |
| 75 | CF₃SO₂O— | H | H | H | H | F | F | H | 2 | m.p. 64~65° C. |
| 76 | CH₃SO₂O— | H | H | H | H | F | F | H | 2 | |
| 77 | F | CF₃ | H | H | H | F | F | H | 2 | $n_D^{20.9}$ 1.5072 |
| 78 | CH₃O— | CH₃O | H | H | H | F | F | H | 2 | $n_D^{20.0}$ 1.5519 |
| 79 | Cl | H | CH₃O | H | H | F | F | H | 2 | m.p. 68~70° C. |
| 80 | t-C₄H₉ | H | CH₃O | H | H | F | F | H | 2 | |
| 81 | H | H | CH₃O | H | t-C₄H₉ | F | F | H | 2 | |
| 82 | CH₃S— | H | H | H | H | F | F | H | 2 | m.p. 87~88° C. |
| 83 | n-C₃H₇S— | H | H | H | H | F | F | H | 2 | $n_D^{20.5}$ 1.5652 |
| 84 | H | n-C₃H₇S | H | H | H | F | F | H | 2 | $n_D^{20.5}$ 1.5623 |
| 85 | —OC(CH₃)₂CH₂CH₂— | | H | H | H | F | F | H | 2 | $n_D^{18.8}$ 1.5486 |
| 86 | —CH₂CH₂C(CH₃)₂O— | | H | H | H | F | F | H | 2 | $n_D^{20.0}$ 1.5442 |
| 87 | F | F | F | F | F | F | F | H | 2 | $n_D^{19.8}$ 1.4964 |
| 88 | CF₃ | F | F | F | F | F | F | H | 2 | $n_D^{20.0}$ 1.4837 |
| 89 | F | Cl | F | H | Cl | F | F | H | 2 | |
| 90 | CF₃ | H | H | H | H | F | H | H | 2 | m.p. 67~69° C. |
| 91 | CF₃ | H | H | H | H | Cl | H | H | 2 | m.p. 40~42° C. |
| 92 | CF₃O— | H | H | H | H | F | H | H | 2 | m.p. 49~51° C. |
| 93 | CF₃O— | H | H | H | H | Cl | H | H | 2 | $n_D^{20.0}$ 1.5317 |
| 94 | CF₃O— | H | H | H | H | Br | H | H | 2 | $n_D^{20.0}$ 1.5406 |
| 95 | CF₃O— | H | H | H | H | CH₃ | H | H | 2 | $n_D^{20.0}$ 1.5240 |
| 96 | CF₃O— | H | H | H | H | CF₃ | H | H | 2 | $n_D^{20.0}$ 1.4918 |
| 97 | CF₃O— | H | H | H | H | F | H | 4-F | 2 | $n_D^{20.0}$ 1.5106 |
| 98 | CF₃O— | H | H | H | H | F | Cl | H | 2 | $n_D^{19.9}$ 1.5157 |
| 99 | CF₃O— | H | H | H | H | Cl | Cl | H | 2 | $n_D^{20.0}$ 1.5298 |
| 100 | CF₃O— | H | H | H | H | Cl | Cl | 4-Cl | 2 | $n_D^{20.0}$ 1.5396 |
| 101 | CF₃O— | H | H | H | H | CH₃O | CH₃O | H | 2 | $n_D^{20.1}$ 1.5222 |
| 102 | CF₃O— | H | H | H | H | F | F | 4-F | 2 | m.p. 59~61° C. |
| 103 | H | CF₃O | H | H | H | F | F | H | 2 | $n_D^{20.0}$ 1.5040 |
| 104 | t-C₄H₉O— | H | H | H | H | F | F | H | 2 | $n_D^{20.0}$ 1.5338 |
| 105 | —CH=CH—CH=CH— | | H | H | H | F | F | H | 2 | $n_D^{19.4}$ 1.6011 |
| 106 | CF₃O— | H | H | H | H | CF₃ | F | H | 2 | $n_D^{20.0}$ 1.4818 |

TABLE 2

| Compound | ¹H-NMR (CDCl₃, δ ppm) |
|---|---|
| 19 | 2.03 to 2.32 (2H, m), 4.14 to 4.31 (3H, m), 4.50 to 4.63 (2H, m), 6.78 to 7.45 (7H, m), 7.97 (1H, s), 8.28 (1H, s) |
| 33 | 1.98 to 2.32 (2H, m), 4.06 to 4.31 (3H, m), 4.47 to 4.66 (2H, m), 6.88 to 7.50 (6H, m), 7.98 (1H, d, J=1.8Hz), 8.24 (1H, d, J=3.1Hz) |
| 43 | 1.97 to 2.31 (2H, m), 4.05 to 4.30 (3H, m), 4.43 to 4.67 (2H, m), 4.80 to 5.12 (1H, m), 6.68 to 7.52 (7H, m) |

Example 3

(Preparation of formulations)

(1) Preparation of granule

Five parts by weight of Compound 1 was uniformly mixed with 35 parts by weight of bentonite, 57 parts by weight of talc, 1 part by weight of Neopelex powder (trade name, produced by Kao K.K.) and 2 parts by weight of sodium lignosulfonate, and then, the mixture was kneaded with addition of a small amount of water, followed by granulation and drying, to obtain a granule.

(2) Preparation of wettable powder

Ten parts by weight of Compound 1 was uniformly mixed with 70 parts by weight of kaolin, 18 parts by weight of white carbon, 1.5 parts by weight of Neopelex powder (trade name, produced by Kao K.K.) and 0.5 part by weight of Demol (trade name, produced by Kao K.K.), and then the mixture was pulverized to obtain a wettable powder.

(3) Preparation of emulsifiable concentrate

Twenty parts by weight of Compound 1 was uniformly mixed with 70 parts by weight of xylene by adding 10 parts by weight of Toxanone (trade name, produced by Sanyo Kasei Kogyo), and dissolved therein to obtain an emulsifiable concentrate.

(4) Preparation of dustable powder

Five parts by weight of Compound 1 was uniformly mixed with 50 parts by weight of talc and 45 parts by weight of kaolin to obtain a dustable powder.

Example 4

(Tests of effects)

(1) Test of effect on diamond-back moth

The respective wettable powders of the compounds (1) shown in Table 1 prepared as in Example 3 were diluted to 300 ppm, 50 ppm or 10 ppm with water containing a surfactant (0.01%). In these respective chemicals, cabbage leaves (5×5 cm) were dipped for 30 seconds, respectively, and each leaf was put into the respective plastic cups and air dried.

Subsequently, 10 diamond-back moths (3th instar larvae) were placed in the respective cups. The cups were closed and left to stand in a thermostat chamber at 25° C. After 2 days, insecticidal rate was determined by counting living and dead insects in the respective cups.

The insecticidal effect was evaluated by using 4 ranks depending on the range of insecticidal rate (A: 100%, B: less than 100 to 80%, C: less than 80 to 60% and D: less than 60%).

For comparison, the following Comparative compound 1 and Comparative compound 2 described in Japanese Provisional Patent Publication No. 271206/1993 (which corresponds to European Patent Publication No. 0 553 623 A) and Comparative compound 3 described in Japanese Provisional Patent Publication No. 85268/1990 were diluted to 300 ppm, 50 ppm or 10 ppm and their insecticidal rates were evaluated in the same manner.

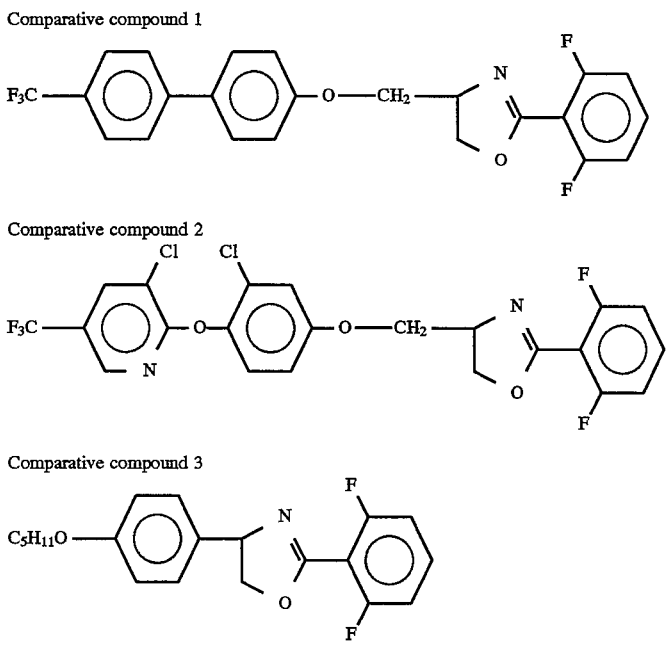

The results are shown in Table 3.

TABLE 3

| | Test of effect on diamond-back moth | | |
|---|---|---|---|
| Compound | Effect | | |
| | ① | ② | ③ |
| 1 | A | A | B |
| 8 | A | A | B |
| 10 | A | A | A |
| 11 | A | A | A |
| 19 | A | A | B |
| 21 | A | A | B |
| 24 | A | A | B |
| 37 | A | A | B |
| 38 | A | A | B |
| 39 | A | A | A |
| 40 | A | A | B |
| 42 | A | A | A |

TABLE 3-continued

Test of effect on diamond-back moth

| Compound | Effect ① | ② | ③ |
|---|---|---|---|
| 43 | A | A | A |
| 49 | A | A | B |
| 52 | A | A | B |
| 53 | A | A | B |
| 54 | A | A | B |
| 55 | A | A | B |
| 57 | A | A | B |
| 65 | A | A | B |
| 77 | A | B | B |
| 87 | A | A | A |
| 88 | A | B | B |
| 93 | A | A | A |
| 94 | A | A | A |
| 95 | A | A | B |
| 97 | A | A | A |
| 98 | A | A | A |
| 99 | A | A | A |
| 103 | A | A | A |
| Comparative 1 | A | B | C |
| Comparative 2 | B | D | D |
| Comparative 3 | D | D | D |

In the Table, ① shows the case where the composition was diluted to 300 ppm, ② shows the case where the composition was diluted to 50 ppm and ③ shows the case where the composition was diluted to 10 ppm, respectively.

(2) Test of effect on common cutworm

The respective wettable powders of the compounds (1) shown in Table 1 prepared as in Example 3 were diluted to 500 ppm or 100 ppm with water containing a surfactant (0.01%). In these respective chemicals, soy bean main leaves were dipped for 30 seconds, respectively and each leaf was put into the respective plastic cups and air-dried.

Subsequently, 10 common cutworms (2th instar larvae) were placed in the respective cups. The cups were closed and left to stand in a thermostat chamber at 25° C. After 2 days, insecticidal rate was determined by counting living and dead insects in the respective cups.

Comparative compounds 1, Comparative compound 2 and Comparative compound 3 described in the above (1) were diluted to 500 ppm or 100 ppm and their insecticidal rates were evaluated in the same manner.

The evaluation results of the insecticidal effect are shown in Table 4 according to the 4 rank evaluation method described in the above (1).

TABLE 4

Test of effect on common cutworm

| Compound | Effect ④ | ⑤ |
|---|---|---|
| 1 | B | B |
| 2 | A | B |
| 3 | A | B |
| 8 | A | A |
| 9 | B | — |
| 10 | A | A |
| 11 | A | A |
| 12 | A | A |
| 13 | A | B |
| 14 | B | C |
| 15 | A | — |
| 18 | A | B |
| 19 | A | B |
| 21 | A | A |
| 22 | B | C |
| 23 | A | A |
| 24 | A | A |
| 25 | A | C |
| 26 | A | B |
| 27 | B | — |
| 31 | A | B |
| 32 | B | C |
| 33 | A | B |
| 34 | C | — |
| 35 | A | A |
| 37 | A | A |
| 38 | A | B |
| 39 | A | A |
| 40 | A | B |
| 42 | A | A |
| 43 | A | A |
| 44 | C | — |
| 49 | A | B |
| 50 | B | B |
| 51 | A | B |
| 52 | A | B |
| 53 | A | B |
| 54 | A | A |
| 55 | A | A |
| 56 | A | A |
| 57 | A | A |
| 58 | C | — |
| 59 | A | B |
| 63 | B | B |
| 64 | A | B |
| 65 | A | A |
| 68 | A | A |
| 69 | A | A |
| 70 | B | C |
| 71 | B | C |
| 73 | C | — |
| 75 | A | A |
| 77 | A | A |
| 79 | A | — |
| 82 | A | A |
| 83 | C | — |
| 84 | C | — |
| 85 | A | C |
| 86 | B | B |
| 87 | A | A |
| 88 | A | A |
| 90 | C | — |
| 91 | C | — |
| 92 | A | B |
| 93 | A | B |
| 94 | A | A |
| 95 | C | C |
| 96 | C | — |
| 97 | A | A |
| 98 | A | A |
| 99 | A | A |
| 102 | B | — |
| 103 | A | A |
| 104 | B | B |
| Comparative 1 | D | D |
| Comparative 2 | D | D |
| Comparative 3 | D | D |

TABLE 4-continued

Test of effect on common cutworm

| Compound | Effect ④ | Effect ⑤ |
|---|---|---|

In the Table, ④ shows the case where the composition was diluted to 500 ppm and ⑤ shows the case where the composition was diluted to 100 ppm, respectively.

(3) Test of effect on two-spotted spider mite egg

The respective wettable powders of the compounds (1) shown in Table 1 prepared as in Example 3 were diluted to 300 ppm with water containing a surfactant (0.01%), and in these respective chemicals, kidney bean leaves (diameter: 20 mm) on which 15 two-spotted spider mite female adults were parasitic for 24 hours to bear eggs thereon and removed were dipped for 10 seconds, respectively.

Subsequently, these leaves were left to stand in a thermostat chamber at 25° C., and after 6 days, egg killing rate was determined by counting not hatched larvae in the respective leaves.

The egg killing effect was evaluated by using 4 ranks depending on the range of egg killing rate (A: 100%, B: less than 100 to 80%, C: less than 80 to 60% and D: less than 60%).

The results are shown in Table 5.

TABLE 5

Test of effect on two-spotted spider mite egg

| Compound | Effect |
|---|---|
| 1 | A |
| 2 | A |
| 3 | A |
| 4 | A |
| 5 | A |
| 6 | A |
| 8 | A |
| 9 | A |
| 10 | A |
| 11 | A |
| 12 | A |
| 13 | A |
| 14 | A |
| 15 | A |
| 17 | A |
| 18 | A |
| 19 | A |
| 21 | A |
| 22 | A |
| 23 | A |
| 24 | A |
| 25 | A |
| 26 | A |
| 27 | A |
| 31 | A |
| 32 | A |
| 33 | A |
| 34 | A |
| 35 | A |
| 37 | A |
| 38 | A |
| 39 | A |
| 40 | A |
| 42 | A |
| 43 | A |
| 44 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 63 | A |
| 64 | A |
| 65 | A |
| 68 | A |
| 69 | A |
| 71 | A |
| 72 | A |
| 73 | A |
| 75 | A |
| 77 | A |
| 79 | A |
| 82 | A |
| 83 | A |
| 84 | A |
| 85 | A |
| 86 | A |
| 87 | A |
| 88 | A |
| 90 | A |
| 91 | A |
| 92 | A |
| 93 | A |
| 94 | A |
| 95 | A |
| 96 | A |
| 97 | A |
| 98 | A |
| 99 | A |
| 100 | A |
| 101 | A |
| 102 | A |
| 103 | A |
| 104 | A |
| 106 | A |

(4) Test of controlling effect on downy mildew (cucumber) (prevention effect)

In plastic flowerpots having a diameter of 6 cm, one cucumber (variety: Sagami Hanshiro) was grown per one flowerpot, and to the young plants at 1.5 leaf stage, the chemicals obtained by diluting the respective wettable powders of the compounds (1) shown in Table 1 prepared as in Example 3 to 500 ppm with water containing a surfactant (0.01%) were sprayed in an amount of 20 ml per one flowerpot, respectively.

After spraying, the cucumbers were grown in a glass greenhouse for 2 days, and then zoosporangia of Pseudoperonospora cubensis collected from infected leaves were sprayed uniformly to the back surfaces of the plant leaves to be inoculated thereinto.

After inoculation, the cucumbers were kept in a dark place at 20° C. for 2 days and grown in a glass greenhouse for 5 days, and the degree of lesion of downy mildew (cucumber) appeared on the first leaves was examined.

The fungicidal effect was evaluated by using 6 ranks as compared with the degree of lesion in the non-treated district (0: all area is infected, 1: lesion area is about 60%, 2: lesion area is about 40%, 3: lesion area is about 20%, 4: lesion area is 10% or less and 5: no lesion is observed).

The results are shown in Table 6.

TABLE 6

Test of controlling effect on downy mildew (cucumber) (prevention effect)

| Compound | Effect |
|---|---|
| 3 | 4 |
| 7 | 4 |
| Non-treated district | 0 |

The novel oxazoline derivative of the present invention has excellent insecticidal, acaricidal and fungicidal effects.

We claim:

1. An oxazoline compound represented by the formula (I):

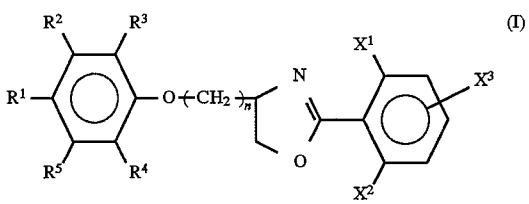

(I)

wherein $R^1$ represents a halogen atom; a hydrogen atom; an alkyl group having 1 to 10 carbon atoms; an alkoxy group having 1 to 8 carbon atoms; a haloalkyl group having 1 to 4 carbon atoms; a haloalkoxy group having 1 to 4 carbon atoms; a phenyl group which is unsubstituted or substituted by a halogen atom, a haloalkyl group having 1 to 4 carbon atoms or a haloalkoxy group having 1 to 4 carbon atoms; a phenoxy group which is unsubstituted or substituted by a halogen atom; a haloalkyl group having 1 to 4 carbon atoms or a haloalkoxy group having 1 to 4 carbon atoms; a benzyl group which is unsubstituted or substituted by a halogen atom; a benzyloxy group which is unsubstituted or substituted by a halogen atom; an alkyl group having 1 to 4 carbon atoms substitituted by an alkoxy group having 1 to 4 carbon atoms; a nitro group; a cyanomethyloxy group; a haloalkylsulfonyloxy group having 1 to 4 carbon atoms; an alkylsulfonyloxy group having 1 to 4 carbon atoms; or an alkylthio group having 1 to 4 carbon atoms; $R^2$ represents a hydrogen atom, a fluorine atom; a chlorine atom; a bromine atom; an alkyl group having 1 or 2 carbon atoms; a haloalkyl group having 1 or 2 carbon atoms; an alkoxy group having 1 to 4 carbon atoms; an alkylthio group having 1 to 4 carbon atoms; or a haloalkoxy group having 1 to 4 carbon atoms; or $R^1$ and $R^2$ may be combined to form an unsaturated 6-membered ring or $R^1$ and $R^2$ may be combined to form a saturated 6-membered ring which ring may have an oxygen atom and is unsubstituted or substituted by 1 or 2 methyl groups; $R^3$ represents a hydrogen atom; a fluorine atom; a chlorine atom, a bromine atom; or an alkoxy group having 1 or 2 carbon atoms; $R^4$ represents a hydrogen atom; an alkyl group having 1 or 2 carbon atoms; a fluorine atom; a chlorine atom; or a bromine atom; $R^5$ represents a hydrogen atom; a fluorine atom; a chlorine atom; a bromine atom; or an alkoxy group having 1 to 6 atoms; $X^1$ represents a halogen atom; an alkyl group having 1 to 4 carbon atoms; a haloalkyl group having 1 to 4 carbon atoms; or an alkoxy group having 1 to 4 carbon atoms; $X^2$ represents a fluorine atom; a chlorine atom; a bromine atom; a hydrogen atom; or an alkoxy group having 1 to 4 carbon atoms; $X^3$ represents a hydrogen atom; a fluorine atom; a chlorine atom; or a bromine atom; and n represents an integer of 2 to 5.

2. The compound according to claim 1, wherein $R^1$ is selected from the group consisting of a halogen atom; a hydrogen atom; an alkyl group having 1 to 8 carbon atoms; an alkoxy group having 1 to 6 carbon atoms; a haloalkyl group having 1 to 4 carbon atoms; a haloalkoxy group having 1 to 4 carbon atoms; a substituted or unsubstituted phenyl group; a substituted or unsubstituted phenoxy group; a substituted or unsubstituted benzyl group; a substituted or unsubstituted benzyloxy group; an alkyl group substituted by an alkoxy group having 1 or 2 carbon atoms; a nitro group; a cyanomethyloxy group; a haloalkylsulfonyloxy group having 1 to 4 carbon atoms; an alkylsulfonyloxy group; and an alkylthio group having 1 to 4 carbon atoms.

3. The compound according to claim 2, wherein $R^1$ is selected from the group consisting of a halogen atom; a hydrogen atom; an alkyl group having 1 to 6 carbon atoms; an alkoxy group having 4 to 6 carbon atoms; a trifluoromethoxy group; a bromodifluoromethoxy group; a 1,1,2,2-tetrafluoroethoxy group; a 2-chloro-1,1,2-trifluoroethoxy group; a 1,1,2,3,3,3-hexafluoropropoxy group; a phenyl group; a phenyl group substituted by a chlorine atom, a trifluoromethyl group, a trifluoromethoxy group, a difluoromethoxy group or a 2-chloro-1,1,2-trifluoroethoxy group; a phenoxy group; a phenoxy group substituted by a chlorine atom, a fluorine atom, a trifluoromethyl group or a trifluoromethoxy group; a benzyl group; a benzyloxy group; an ethyl group substituted by an ethoxy group; a nitro group; a cyanomethyloxy group; a trifluoromethylsulfonyloxy group; an alkylsulfonyloxy group, a methylthio group and a n-propylthio group.

4. The compound according to claim 1, wherein $R^2$ is selected from the group consisting of a chlorine atom; a bromine atom; a fluorine atom; a methyl group; a trifluoromethyl group; a methoxy group; a propylthio group and a trifluoromethoxy group.

5. The compound according to claim 1, wherein $R^1$ and $R^2$ are combined to form an unsaturated 6-membered ring or $R^1$ and $R^2$ are combined to form a saturated 6-membered ring which may have an oxygen atom and may be substituted by one or two methyl groups.

6. The compound according to claim 5, wherein $R^1$ and $R^2$ is combined to form —OC(CH$_3$)$_2$CH$_2$CH$_2$—, —CH$_2$CH$_2$C(CH$_3$)$_2$O— or —CH=CH—CH=CH—.

7. The compound according to claim 1, wherein the compound is selected from the group consisting of:

a compound in which $R^1$ is a halogen atom, $X^1$ and $X^2$ are each a fluorine atom, a chlorine atom or a bromine atom, $R^2$ to $R^5$ and $X^3$ are hydrogen atoms, and n is 2;

a compound in which $R^1$ to $R^5$ and $X^3$ are hydrogen atoms, $X^1$ and $X^2$ are each a fluorine atom, a chlorine atom or a bromine atom, and n is 2;

a compound in which $R^1$ to $R^5$ and $X^3$ are hydrogen atoms, $X^1$ and $X^2$ are each a fluorine atom, a chlorine atom or a bromine atom, and n is 3;

a compound in which $R^1$ is a halogen atom, $R^3$, $X^1$ and $X^2$ are each a fluorine atom, a chlorine atom or a bromine atom, $R^2$, $R^4$, $R^5$ and $X^3$ are hydrogen atoms, and n is 2;

a compound in which $R^1$ is an alkyl group having 1 to 10 carbon atoms, $R^2$ to $R^5$ and $X^3$ are hydrogen atoms, $X^1$ and $X^2$ are each a fluorine atom, a chlorine atom or a bromine atom, and n is 2;

a compound in which $R^1$ is an alkoxy group having 1 to 8 carbon atoms, $R^2$ to $R^5$ and $X^3$ are hydrogen atoms, $X^1$ and $X^2$ are each a fluorine atom, a chlorine atom or a bromine atom, and n is 2;

a compound in which $R^1$ is a halogen atom, $R^2$, $X^1$ and $X^2$ are each a fluorine atom, a chlorine atom or a bromine atom, $R^3$ to $R^5$ and $X^3$ are hydrogen atoms, and n is 2;

a compound in which $R^1$ is a haloalkyl group having 1 to 4 carbon atoms, $R^2$ to $R^5$ and $X^3$ are hydrogen atoms, $X^1$ and $X^2$ are each a fluorine atom, a chlorine atom or a bromine atom, and n is 2;

a compound in which $R^1$ is a haloalkoxy group having 1 to 4 carbon atoms, $R^2$ to $R^5$ and $X^3$ are hydrogen atoms, $X^1$ and $X^2$ are each a fluorine atom, a chlorine atom or a bromine atom, and n is 2;

a compound in which $R^1$ is a phenyl group, $R^2$ to $R^5$ and $X^3$ are hydrogen atoms, $X^1$ and $X^2$ are each a fluorine atom, a chlorine atom or a bromine atom, and n is 2;

a compound in which $R^1$ is a phenoxy group, $R^2$ to $R^5$ and $X^3$ are hydrogen atoms, $X^1$ and $X^2$ are each a fluorine atom, a chlorine atom or a bromine atom, and n is 2;

a compound in which $R^1$ is a phenoxy group, $R^2$, $R^5$ and $X^3$ are hydrogen atoms, $R^3$, $X^1$ and $X^2$ are each a fluorine atom, a chlorine atom or a bromine atom, $R^4$ is an alkyl group having 1 to 2 carbon atoms, and n is 2;

a compound in which $R^1$ is a benzyl group, $R^2$ to $R^5$ and $X^3$ are hydrogen atoms, $X^1$ and $X^2$ are each a fluorine atom, a chlorine atom or a bromine atom, and n is 2;

a compound in which $R^1$ is an alkyl group having 1 to 4 carbon atoms which is substituted by an alkoxy group having 1 to 4 carbon atoms, $R^2$ to $R^5$ and $X^3$ are hydrogen atoms, $X^1$ and $X^2$ are each a fluorine atom, a chlorine atom or a bromine atom, and n is 2;

a compound in which $R^1$ is a haloalkoxy group having 1 to 4 carbon atoms, $R^2$ to $R^4$ and $X^3$ are hydrogen atoms, $R^5$, $X^1$ and $X^2$ are each a fluorine atom, a chlorine atom or a bromine atom, and n is 2;

a compound in which $R^1$ is a haloalkoxy group having 1 to 4 carbon atoms, $R^3$ to $R^5$ and $X^3$ are hydrogen atoms, $R^2$, $X^1$ and $X^2$ are each a fluorine atom, a chlorine atom or a bromine atom, and n is 2;

a compound in which $R^1$ is a haloalkoxy group having 1 to 4 carbon atoms, $R^3$, $R^4$ and $X^3$ are hydrogen atoms, $R^2$, $R^5$, $X^1$ and $X^2$ are each a fluorine atom, a chlorine atom or a bromine atom, and n is 2;

a compound in which $R^1$ is a halogen atom, $R^3$, $X^1$ and $X^2$ are each a fluorine atom, a chlorine atom or a bromine atom, $R^2$, $R^4$, $R^5$ and $X^3$ are hydrogen atoms, and n is 2;

a compound in which $R^1$ is a haloalkyl group having 1 to 4 carbon atoms, $R^2$, $R^4$, $R^5$ and $X^3$ are hydrogen atoms, $R^3$, $X^1$ and $X^2$ are each a fluorine atom, a chlorine atom or a bromine atom, and n is 2;

a compound in which $R^1$ is a haloalkoxy group having 1 to 4 carbon atoms, $R^2$, $R^4$, $R^5$ and $X^3$ are hydrogen atoms, $R^3$, $X^1$ and $X^2$ are each a fluorine atom, a chlorine atom or a bromine atom, and n is 2;

a compound in which $R^1$ is a phenoxy group, $R^2$, $R^4$, $R^5$ and $X^3$ are hydrogen atoms, $R^3$, $X^1$ and $X^2$ are each a fluorine atom, a chlorine atom or a bromine atom, and n is 2;

a compound in which $R^1$ is a n alkyl group having 1 to 10 carbon atoms, $R^2$, $R^4$, $R^5$ and $X^3$ are hydrogen atoms, $R^3$, $X^1$ and $X^2$ are each a fluorine atom, a chlorine atom or a bromine atom, and n is 2;

a compound in which $R^1$ is a haloalkyl group having 1 to 4 carbon atoms, $R^2$ to $R^5$ and $X^3$ are hydrogen atoms, $X^1$ and $X^2$ are each a fluorine atom, a chlorine atom or a bromine atom, and n is 3;

a compound in which $R^1$ is a haloalkyl group having 1 to 4 carbon atoms, $R^2$ to $R^5$ and $X^3$ are hydrogen atoms, $X^1$ and $X^2$ are each a fluorine atom, a chlorine atom or a bromine atom, and n is 5;

a compound in which $R^1$ is a phenyl group, $R^2$ is an alkyl group having 1 to 2 carbon atoms, $R^5$ is an alkyl group having 1 to 4 carbon atoms, $R^3$, $R^4$ and $X^3$ are hydrogen atoms, $X^1$ and $X^2$ are each a fluorine atom, a chlorine atom or a bromine atom, and n is 2;

a compound in which $R^1$ is a benzyloxy group, $R^2$ to $R^5$ and $X^3$ are hydrogen atoms, $X^1$ and $X^2$ are each a fluorine atom, a chlorine atom or a bromine atom, and n is 2;

a compound in which $R^1$ is a nitro group, $R^2$ to $R^5$ and $X^3$ are hydrogen atoms, $X^1$ and $X^2$ are each a fluorine atom, a chlorine atom or a bromine atom, and n is 2;

a compound in which $R^1$ is a haloalkylsulfonyloxy group having 1 to 4 carbon atoms, $R^2$ to $R^5$ and $X^3$ are hydrogen atoms, $X^1$ and $X^2$ are each a fluorine atom, a chlorine atom or a bromine atom, and n is 2;

a compound in which $R^1$ is a halogen atom, $X^1$ and $X^2$ are each a fluorine atom, a chlorine atom or a bromine atom, $R^2$ is a haloalkyl group having 1 to 2 carbon atoms, $R^3$ to $R^5$ and $X^3$ are hydrogen atoms, and n is 2;

a compound in which $R^1$ is a halogen atom, $X^1$ and $X^2$ are each a fluorine atom, a chlorine atom or a bromine atom, $R^2$, $R^4$, $R^5$ and $X^3$ are hydrogen atoms $R^3$ is an alkoxy group having 1 to 2 carbon atoms, and n is 2;

a compound in which $R^1$ is an alkylthio group having 1 to 4 carbon atoms, $X^1$ and $X^2$ are each a fluorine atom, a chlorine atom or a bromine atom, $R^2$ to $R^5$ and $X^3$ are hydrogen atoms, and n is 2;

a compound in which $R^1$, $R^3$ to $R^5$ and $X^3$ are hydrogen atoms, $R^2$ is an alkylthio group having 1 to 4 carbon atoms, $X^1$ and $X^2$ are each a fluorine atom, a chlorine atom or a bromine atom, and n is 2;

a compound in which $R^1$ and $R^2$ form a saturated 6-membered ring or unsaturated 6-membered ring which may contain an oxygen atom and may be substituted by one or two methyl groups, $R^3$ to $R^5$ and $X^3$ are hydrogen atoms, $X^1$ and $X^2$ are each a fluorine atom, a chlorine atom or a bromine atom, and n is 2;

a compound in which $R^1$ is a halogen atom, $R^2$, $R^3$, $R^5$, $X^1$ and $X^2$ are each a fluorine atom, a chlorine atom or a bromine atom, $R^4$ is an alkyl group having 1 to 2 carbon atoms, $X^3$ is a hydrogen atom, and n is 2;

a compound in which $R^1$ is a haloalkoxy group having 1 to 4 carbon atoms, $R^2$, $R^3$, $R^5$, $X^1$ and $X^2$ are each a fluorine atom, a chlorine atom or a bromine atom, $R^4$ is an alkyl group having 1 to 2 carbon atoms, $X^3$ is a hydrogen atom, and n is 2;

a compound in which $R^1$ is a haloalkoxy group having 1 to 4 carbon atoms, $R^2$ to $R^5$ and $X^3$ are hydrogen atoms, $X^1$ is a haloalkyl group having 1 to 4 carbon atoms, $X^2$ is a fluorine atom, a chlorine atom or a bromine atom, and n is 2;

a compound in which $R^1$ is a haloalkoxy group having 1 to 4 carbon atoms, $R^2$ to $R^5$ and $X^2$ are hydrogen atoms, $X^1$ is an alkyl group having 1 to 4 carbon atoms, $X^3$ is a fluorine atom, a chlorine atom or a bromine atom, and n is 2;

a compound in which $R^1$ is a haloalkoxy group having 1 to 4 carbon atoms, $R^2$ to $R^5$ are hydrogen atoms, $X^1$ to $X^3$ are each a fluorine atom, a chlorine atom or a bromine atom, and n is 2;

a compound in which $R^1$ is a haloalkoxy group having 1 to 4 carbon atoms, $R^2$ to $R^5$ and $X^3$ are hydrogen atoms, $X^1$ and $X^2$ are alkoxy groups having 1 to 4 carbon atoms, and n is 2;

a compound in which $R^1$ is a haloalkoxy group having 1 to 4 carbon atoms, $R^2$ to $R^5$ and $X^1$ to $X^3$ are hydrogen atoms, and n is 2; and a compound in which $R^1$, $R^3$ to $R^5$ and $X^3$ are hydrogen atoms, $R^2$ is a haloalkoxy group having 1 to 4 carbon atoms, $X^1$ and $X^2$ are each a fluorine atom, a chlorine atom or a bromine atom, and n is 2.

8. The compound according to claim 1, wherein the compound is selected from the group consisting of:

2-(2,6-difluorophenyl)-4-{2-(4-chlorophenoxy)ethyl}-2-oxazoline, 2-(2,6-difluorophenyl)-4-{2-(4-bromophenoxy)ethyl}-2-oxazoline, 2-(2,6-difluorophenyl)-4-(2-phenoxyethyl)-2-oxazoline, 2-(2,6-difluophenyl)-4-(3-phenoxypropyl)-2-oxazoline, 2-(2,6-difluophenyl)-4-{2-(2-chlorophenoxy)ethyl}-2-oxazoline, 2-(2,6-difluorophenyl)-4-{2-(4-methylphenoxy)ethyl}-2-oxazoline, 2-(2,6-difluorophenyl)-4-{2-(4-methoxyphenoxy)ethyl}-2-oxazoline, 2-(2,6-difluorophenyl)-4-{2-(3,4-dichlorophenoxy)ethyl}-2-oxazoline, 2-(2,6-difluorophenyl)-4-{2-(4-tert-butylphenoxy)ethyl}-2-oxazoline, 2-(2,6-difluorophenyl)-4-{2-(4-trifluoromethylphenoxy)ethyl}-2-oxazoline, 2-(2,6-difluorophenyl)-4-{2-(4-trifluoromethoxyphenoxy)ethyl}-2-oxazoline, 2-(2,6-difluorophenyl)-4-{2-(4-phenylphenoxy)ethyl}-2-oxazoline, 2-(2,6-difluorophenyl)-4-{2-(4-phenoxyphenoxy)ethyl}-2-oxazoline, 2-(2,6-difluorophenyl)-4-{2-{2-chloro-4-(4-chlorophenoxy)-6-methylphenoxy}ethyl}-2-oxazoline, 2-(2,6-difluorophenyl)-4-{2-{2-chloro-4-(4-chlorobenzyl)-6-methylphenoxy}ethyl}-2-oxazoline, 2-(2,6-difluorophenyl)-4-{2-{4-(2-ethoxyethyl)phenoxy}-ethyl}-2-oxazoline, 2-(2,6-difluorophenyl)-4-{2-{4-(4-chlorophenoxy)phenoxy}-ethyl}-2-oxazoline, 2-(2,6-difluorophenyl)-4-{2-{4-(4-fluorophenoxy)phenoxy}-ethyl}-2-oxazoline, 2-(2,6-difluorophenyl)-4-{2-{4-(4-trifluoromethylphenoxy)phenoxy}-ethyl}-2-oxazoline, 2-(2,6-difluorophenyl)-4-{2-{4-(2-chloro-4-trifluoromethylphenoxy)phenoxy}-ethyl}-2-oxazoline, 2-(2,6-difluorophenyl)-4-{2-(2,4-difluorophenoxy)ethyl}-2-oxazoline, 2-(2,6-difluorophenyl)-4-{2-{4-(4-trifluoromethoxyphenoxy)phenoxy}ethyl}-2-oxazoline, 2-(2,6-difluorophenyl)-4-{2-(4-n-butoxyphenoxy)ethyl}-2-oxazoline, 2-(2,6-difluorophenyl)-4-{2-(4-n-hexylphenoxy)ethyl}-2-oxazoline, 2-(2,6-difluorophenyl)-4-{2-(4-n-hexyloxyphenoxy)ethyl}-2-oxazoline, 2-(2,6-difluorophenyl)-4-{2-(4-difluoromethoxyphenoxy)ethyl}-2-oxazoline, 2-(2,6-difluorophenyl)-4-{2-(4-bromodifluoromethoxyphenoxy)ethyl}-2-oxazoline, 2-(2,6-difluorophenyl)-4-{2-{4-(1,2,2-trifluoroethoxy)phenoxy}ethyl}-2-oxazoline, 2-(2,6-difluorophenyl)-4-{2-{4-(1,1,2,2-tetrafluoroethoxy)phenoxy}ethyl}-2-oxazoline, 2-(2,6-difluorophenyl)-4-{2-{4-(2,2,2-trifluoroethoxy)phenoxy}ethyl}-2-oxazoline, 2-(2,6-difluorophenyl)-4-{2-{4-(2-chloro-1,1,2-trifluoroethoxy)-phenoxy}ethyl}-2-oxazoline, 2-(2,6-difluorophenyl)-4-{2-{4-(1,1,2,3,3,3-hexafluoropropoxy)phenoxy}ethyl}-2-oxazoline, 2-(2,6-difluorophenyl)-4-{2-(3,5-dichloro-4-difluoromethoxyphenoxy)ethyl)-2-oxazoline, 2-(2,6-difluorophenyl)-4-{2-{3,5-dichloro-4-{2-chloro-1,1,2-trifluoroethoxy)phenoxy}ethyl}-2-oxazoline, 2-(2,6-difluorophenyl)-4-{2-(4-fluorophenoxy)ethyl}-2-oxazoline, 2-(2,6-difluorophenyl)-4-{2-(4-iodophenoxy)ethyl}-2-oxazoline, 2-(2,6-difluorophenyl)-4-{2-(2,4-dichlorophenoxy)ethyl}-2-oxazoline, 2-(2,6-difluorophenyl)-4-{2-(4-bromo-2-fluorophenoxy)ethyl}-oxazoline, 2-(2,6-difluorophenyl)-4-{2-(2-chloro-4-trifluoromethylphenoxy)ethyl}-2-oxazoline, 2-(2,6-difluorophenyl)-4-{2-(2-chloro-4-trifluoromethoxyphenoxy)ethyl}-2-oxazoline, 2-(2,6-difluorophenyl)-4-{2-(2-chloro-4-phenoxyphenoxy)-ethyl}-2-oxazoline, 2-(2,6-difluorophenyl)-4-{2-{2-chloro-4-(4-chlorophenoxy)phenoxy}-ethyl}-2-oxazoline 2-(2,6-difluorophenyl)-4-{2-(2-chloro-4-tert-butylphenoxy)ethyl}-2-oxazoline, 2-(2,6-difluorophenyl)-4-{2-{4-(2,3,4,5,6-pentafluorophenoxy)phenoxy}ethyl}-2-oxazoline, 2-(2,6-difluorophenyl)-4-{3-(4-trifluoromethylphenoxy)propyl}-2-oxazoline, 2-(2,6-difluorophenyl)-4-{5-(4-trifluoromethylphenoxy)pentyl}-2-oxazoline, 2-(2,6-difluorophenyl)-4-{2-{4-(4-trifluoromethylphenyl)phenoxy}ethyl}-2-oxazoline, 2-(2,6-difluorophenyl)-4-{2-{4-difluoromethoxyphenyl)phenoxy}ethyl}-2-oxazoline, 2-(2,6-difluorophenyl)-4-{2-{4-(4-trifluoromethoxYyphenyl)phenoxy}ethyl}-2-oxazoline, 2-(2,6-difluorophenyl)-4-{2-{4-{4-(1,1,2-trifluo-2-chloroethoxy)phenyl}phenoxy}ethyl}-2-oxazoline, 2-(2,6-difluorophenyl)-4-{2-{4-(4-chlorophenyl)-3,5-dimethylphenoxy}ethyl}-2-oxazoline, 2-(2,6-difluorophenyl)-4-{2-(4-benzyloxyphenoxy)ethyl)-2-oxazoline, 2-(2,6-difluorophenyl)-4-{2-{4-(4-chlorobenzyloxy)phenoxy}ethyl}-2-oxazoline, 2-(2,6-difluorophenyl)-4-(2-{4-nitrophenoxy)ethyl}-2-oxazoline, 2-(2,6-difluorophenyl)-4-{2-(4-cyanomethoxyphenoxy)ethyl}-2-oxazoline, 2-(2,6-difluorophenyl)-4-{2-(4-trifluoromethanesulfonyloxyphenoxy)ethyl}phenoxy)ethyl}-2-oxazoline, 2-(2,6-difluorophenyl)-4-{2-(3,4-dimethoxyphenoxy)ethyl}-2-oxazoline, 2-(2,6-difluorophenyl)-4-{2-(4-chloro-2-methoxyphenoxy)ethyl}-2-oxazoline, 2-(2,6-difluorophenyl)-4-{2-(methylthiophenoxy)ethyl}-2-oxazoline, 2-(2,6-difluorophenyl)-4-{2-(4-n-propylthiophenoxy)ethyl}-2-oxazoline, 2-(2,6-difluorophenyl)-4-{2-(3-n-propylthiophenoxy)ethyl}-2-oxazoline, 2-(2,6-difluorophenyl)-4-{2-(2,2-dimethyl-3,4-dihydro-2H-chromen-6-yloxy)ethyl}-2-oxazoline, 2-(2,6-difluorophenyl)-4-{2-(2,2-dimethyl-3,4-dihydro-2H-chromen-7-yloxy)ethyl}-2-oxazoline, 2-(2,6-difluorophenyl)-4-{2-(2,3,4,5,6-pentafluorophenoxy)ethyl}-2-oxazoline, 2-(2,6-difluorophenyl)-4-{2-(2,3,5,6-tetrafluoro-4-trifluoromethylphenoxy)ethyl}-2-oxazoline, 2-(2-difluorophenyl)-4-{2-(4-trifluoromethylphenoxy)ethyl}-2-oxazoline, 2-(2-chlorophenyl)-4-{2-(4-trifluoromethylphenoxy)ethyl}-2-oxazoline, 2-(2-fluorophenyl)-4-{2-(4-trifluoromethoxyphenoxy)ethyl}-2-oxazoline, 2-(2-chlorophenyl)-4-{2-(4-trifluoromethoxyphenoxy)ethyl}-2-oxazoline, 2-(2-bromophenyl)-4-{2-(4-trifluoromethoxyphenoxy)ethyl}-2-oxazoline, 2-(2-methylphenyl)-4-{2-(4-trifluoromethoxyphenoxy)ethyl}-2-oxazoline, 2-(2-trifluoromethylphenyl)-4-{2-(4-trifluoromethoxyphenoxy)ethyl}-2-oxazoline, 2-(2,4-difluorophenyl)-4-{2-(4-trifluoromethoxyphenoxy)ethyl}-2-oxazoline, 2-(2-chloro-6-fluorophenyl)-4-{2-(4-trifluoromethoxyphenoxy)ethyl}-2-oxazoline, 2-(2,6-dichlorophenyl)-4-{2-(4-trifluoromethoxyphenoxy)ethyl}-2-oxazoline, 2-(2,4,6-trichlorophenyl)-4-{2-(4-trifluoromethoxyphenoxy)ethyl}-2-oxazoline, 2-(2,6-dimethylphenyl)-4-{2-(4-trifluoromethoxyphenoxy)ethyl}-2-oxazoline, 2-(2,4,6-trifluorophenyl)-4-{2-(4-trifluoromethoxyphenoxy)ethyl}-2-oxazoline, 2-(2,6-difluorophenyl)-4-{2-(3-trifluoromethoxyphenoxy)ethyl}-2-oxazoline, 2-(2,6-difluorophenyl)-4-{2-(4-tert-butoxyphenoxy)ethyl}-2-oxazoline, 2-(2,6-difluorophenyl)-4-{2-(2-naphthyloxy)ethyl}-2-oxazoline and 2-(2-fluoro-6-trifluoromethylphenyl)-4-{2-(4-trifluoromethoxyphenoxy)ethyl}-2-oxazoline.

9. An insecticide, acaricide, or fungicide composition comprising the compound represented by the formula (I) according to claim 1 as an active ingredient and an insecticidally, acaricidally or fungicidally effective carrier.

* * * * *

UNITED STATES PATENT AND TRADEMARK OFFICE
CERTIFICATE OF CORRECTION

Page 1 of 2

PATENT NO. : 5,639,771
DATED : June 17, 1997
INVENTOR(S) : Tokio OBATA et al.

It is certified that error appears in the above-identified patent and that said Letters Patent is hereby corrected as shown below:

Claim 1, column 35, line 39, "substitituted" should read --substituted--.

Claim 7, column 37, line 62, "a n" should read --an--.

Claim 7, column 38, line 30, after "hydrogen atom" insert --,--.

Claim 8, column 39, line 22, "(2,6-difluophenyl)" should read --(2,6-difluorophenyl)--.

Claim 8, column 39, line 23, "(2,6-difluophenyl)" should read --(2,6-difluorophenyl)--.

Claim 8, column 40, line 30, "ethyl}-oxazoline," should read --ethyl}-2-oxazoline,--.

Claim 8, column 40, line 38, after "oxazoline", insert --,--.

UNITED STATES PATENT AND TRADEMARK OFFICE
CERTIFICATE OF CORRECTION

PATENT NO. : 5,639,771
DATED : June 17, 1997
INVENTOR(S) : Tokio OBATA et al.

It is certified that error appears in the above-identified patent and that said Letters Patent is hereby corrected as shown below:

Claim 8, column 40, line 53, "trifluoromethoxYyphenyl)" should read --trifluoromethoxyphenyl)--.

Claim 8, column 41, line 3, after "2-oxazoline", insert the following paragraph:
--2-(2,6-difluorophenyl)-4-{2-(4-fluoro-3-trifluoromethylphenoxy)ethyl}-2-oxazoline,--.

Signed and Sealed this

Twenty-third Day of February, 1999

Q. TODD DICKINSON

*Attest:*

*Attesting Officer*         *Acting Commissioner of Patents and Trademarks*

UNITED STATES PATENT AND TRADEMARK OFFICE
CERTIFICATE OF CORRECTION

PATENT NO.: 5,639,771

DATED: March 23, 1999

INVENTOR(S): Tokio OBATA et al.

It is certified that an error appears in the above-identified patent and that said Letters Patent is hereby corrected as shown below:

IN THE CLAIMS:

Claim 8, column 41, after line 3, insert the following new paragraph:

--2-(2,6-difluorophenyl)-4-{2-(4-fluoro-3-trifluoromethylphenoxy)ethyl}-2-oxazoline,--.

Signed and Sealed this

Eleventh Day of May, 1999

Attest:

Q. TODD DICKINSON

*Attesting Officer*

*Acting Commissioner of Patents and Trademarks*